(12) United States Patent
Boden et al.

(10) Patent No.: US 7,537,902 B2
(45) Date of Patent: May 26, 2009

(54) METHODS AND KITS USING A MOLECULAR INTERACTION BETWEEN A SMURF-1 WW DOMAIN AND LIM MINERALIZATION PROTEIN ISOFORMS

(75) Inventors: Scott D. Boden, Atlanta, GA (US); Sreedhara Sangadala, Dallas, GA (US)

(73) Assignee: Emory University, Atlanta, GA (US)

( * ) Notice: Subject to any disclaimer, the term of this patent is extended or adjusted under 35 U.S.C. 154(b) by 74 days.

(21) Appl. No.: 11/607,348

(22) Filed: Dec. 1, 2006

(65) Prior Publication Data

US 2007/0190572 A1     Aug. 16, 2007

Related U.S. Application Data

(63) Continuation-in-part of application No. 11/385,612, filed on Mar. 21, 2006, which is a continuation-in-part of application No. 10/399,830, filed as application No. PCT/US01/46044 on Oct. 24, 2001.

(60) Provisional application No. 60/772,322, filed on Feb. 10, 2006, provisional application No. 60/242,794, filed on Oct. 24, 2000.

(51) Int. Cl.
*G01N 33/50* (2006.01)
*G01N 33/53* (2006.01)
*G01N 33/68* (2006.01)

(52) U.S. Cl. ........................... 435/7.1; 436/501

(58) Field of Classification Search ........................ None
See application file for complete search history.

(56) References Cited

U.S. PATENT DOCUMENTS 6,300,127 B1    10/2001    Hair et al.
2006/0134737 A1   6/2006   Beyaert et al.

OTHER PUBLICATIONS

Mohan et al., 2002, J. Endocrinol. 175:19-31.*
Conover et al., 1995, J. Biol. Chem. 270:4395-4400.*
Sangadala et al., "LIM mineralization prtoein-1 potentiates bone morphogenetic protein responsiveness via a novel interaction with smurf1 resulting in decreased ubiquitination of smads", The Journal of Biological Chemistry; Jun. 23, 2006; vol. 281, No. 25, pp. 71212-17219.
LIU et al., "Overexpressed LIM mineralization proteins do not require LIM domains to induce bone", The Journal of Bone and Mineral Research; 2002: vol. 17, No. 3, pp. 406-414.

* cited by examiner

*Primary Examiner*—Elizabeth C. Kemmerer

(57) ABSTRACT

The instant application provides kits and methods for identifying agents which induce or inhibit the osteogenic effect of LMP or BMP proteins. The kits are directed to methods which measure either an amount of a complex between a Smurf protein or a fragment thereof and an LMP protein or a fragment thereof. Alternatively, the kits are directed to methods of measuring an amount of the ubiquitinated Smad protein or a fragment thereof.

12 Claims, 4 Drawing Sheets

A. Purified recombinant Smurf1 and LMP proteins

B. Binding of LMP-1wt and Its mutants to Smurf1

METHODS AND KITS USING A MOLECULAR INTERACTION BETWEEN A SMURF-1 WW DOMAIN AND LIM MINERALIZATION PROTEIN ISOFORMS

CROSS-REFERENCE TO RELATED APPLICATIONS

This application is a continuation-in-part of U.S. application Ser. No. 11/385,612, filed on Mar. 21, 2006, which claims benefit of U.S. Provisional Application 60/772,322 filed on Feb. 10, 2006. The teachings of both of these applications are incorporated herein by reference to the extent they are not inconsistent with the instant disclosure. The U.S. application Ser. No. 11/385,612 is also a continuation-in-part of U.S. application Ser. No. 10/399,830 which entered U.S. national stage on Jul. 25, 2003 from PCT application PCT/US01/46044 filed on Oct. 24, 2001, which claims benefit of U.S. Provisional Application Ser. No. 60/242,794, filed on, Oct. 24, 2000.

STATEMENT REGARDING FEDERALLY FUNDED RESEARCH

This invention was made with government support under Grant No. R01-AR53093 awarded by the National Institutes of Health. The Government has certain rights in the invention.

FIELD OF INVENTION

This invention relates to methods and kits for identification of agents which affect a) the interaction of Smurf1 protein with LMP-1, LMP-3, or LMP-1t, b) the ubiquitination of Smad proteins by Smurf1, or c) the osteogenic effect of BMP or LMP proteins.

BACKGROUND

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, *Genes & Develop.*, 10:1580 (1996). This group of transforming growth factor-beta superfamily secreted proteins has a spectrum of activities in a variety of cell types at different stages of differentiation; differences in physiological activity between these closely related molecules have not been clarified. D. M. Kingsley, *Trends Genet.*, 10:16 (1994).

In addition to extracellular signals, such as the BMPs, intracellular signals or regulatory molecules may also play a role in the cascade of events leading to formation of new bone. One broad class of intracellular regulatory molecules is the LIM proteins, which are so named because they possess a characteristic structural motif known as the LIM domain. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein-protein interactions, through the formation of dimers with identical or different LIM domains, or by binding distinct proteins.

Applicants have previously cloned, sequenced and deduced the amino acid sequence of a human protein, named human LMP-1. The human protein demonstrates enhanced efficacy of bone mineralization in vitro and in vivo. LMP-1 contains an N-terminal PDZ domain and three C-terminal LIM domains. Applicants have also characterized several isoforms of the LMP protein: LMP-1, as discussed above, LMP-2 (which contains a 119 base pair deletion between bp 325 and 444, and a 17 bp insertion at bp 444, compared to LMP-1), LMP-3(which does not have a deletion but has a 17 bp insertion at bp 444, thus resulting in a shift in a reading frame and a stop codon at bp 505), and truncated (short) version of LMP-1, termed HLMP-1s, containing the N-terminal 223 amino acids of the full length hLMP-1, while maintaining osteoinductive activity. Liu et al, *J. Bone Miner. Res;* 17(3): 406-414 (2002), incorporated herein by reference in its entirety.

This short version resulted from a point mutation in one source of a cDNA clone, providing a stop codon which truncated the protein. See U.S. Pat. No. 6,300,127 (Hair), incorporated herein by reference in its entirety. The short version (LMP-1s, also known as LMP-1t or LMP-1(t)) is fully functional when expressed in cell culture and in vivo. In the invention instantly described, inventors have assessed whether a truncated form of human LMP-1 [hLMP-1(t)], lacking the three C-terminal LIM domains, triggers differentiation of pleuripotent myoblastic cells to the osteoblast lineage. It has also been reported that LMP1, LMP-3, and LMP-1t, but not LMP-2, are capable of inducing osteogenic differentiation in non-osseous cells. Accordingly, a 45 amino acid long osteogenic region of LMP1, LMP-3, and LMP-1t was identified. Liu et al (2002).

Even though the precise mechanism of LMP-1 is under investigation, it is generally thought that exogenous BMPs induce bone formation by activating Smad1 and Smad5 proteins. These proteins are targeted for degradation by Smurf1. The LMP-1 protein competes with Smad1, Smad5, and Smad6 proteins for Smurf1 binding thus increasing cellular responsiveness to exogenous BMPs. Sandagala et al., *J. Biol. Chem.* 281(25): 17212-17219 (2006), incorporated herein by reference in its entirety.

Previously, the inventors reported that the osteogenic region of LMP1, LMP-3, and LMP-1t proteins contains two possible candidate sites for interaction with Smurf1, or, more specifically, with a WW-2 motif of Smurf1.

Accordingly, agents which increase binding between the WW-2 motif of Smurf1 and the osteogenic region of the LMP protein will likely cause a decreased ubiquitination of Smad proteins and thus make the Smad proteins more available for the osteogenic signaling cascade caused by BMP. Similarly, agents which disrupt the binding between the WW-2 motif of Smurf1 and the osteogenic region of the LMP protein will likely cause an increased ubiquitination of Smad proteins and thus make the Smad proteins less available for the osteogenic signaling cascade caused by BMP.

Currently, the use of BMPs is feasible for many patients with bone healing needs due to an unexpectedly high dose which is required in humans, which results in a very high cost of BMP therapy. A 15,000 fold higher concentration of BMP-2 is required to induce bone healing in humans (1.5 mg/mL) than in cell culture (100 ng/mL). Thus, there is a need for identification of agents which can affect the osteogenic effect of BMP.

SUMMARY OF INVENTION

The instant invention addresses these and other needs by providing, in one aspect, a method of identifying an agent affecting a binding between an LMP protein and a Smurf1 protein comprising: providing a first composition comprising a first amino acid sequence comprising an amino acid sequence of SEQ. ID NO. 1 ($PPX_1X_2$), a second amino acid sequence comprising an amino acid sequence at least 70% identical to SEQ. ID. NO. 2 (WW domain of SMURF1) and capable of binding the amino acid sequence of SEQ ID NO 1, and the agent; and measuring an amount of a complex formed between the first amino acid sequence and the second amino acid sequence in the first composition.

In another aspect, the invention provides a method of identifying an agent affecting ubiquitination of a Smad protein by Smurf1 comprising: providing a first composition comprising a first amino acid sequence comprising an amino acid sequence of SEQ. ID NO. 1 ($PPX_1X_2$), a second amino acid sequence comprising an amino acid sequence at least 70% identical to SEQ. ID. NO. 2, as shown in Table 2 (WW domain of Smurf1), said second amino acid sequence capable of binding the amino acid sequence of SEQ ID NO 1 and of ubiquitinating the Smad protein, the Smad protein, a source of ubiquitin, a source of ATP, the agent; and measuring an amount of a ubiquitinated Smad protein in the first composition.

In another aspect, the invention provides a method of identifying an agent affecting ubiquitination of a Smad protein by a Smurf1 protein comprising: providing a first composition comprising the Smurf1 protein or a fragment thereof capable of ubiquitinating the Smad protein, a source of ubiquitin, a source of ATP, the Smad protein or a fragment thereof capable of being ubiquitinated by the Smurf1 protein, the agent; and measuring an amount of ubiquitinated Smad protein or the fragment thereof in the first composition.

In another aspect, the invention provides a method of identifying an agent affecting a binding between an LMP protein and a Smurf1 protein comprising: a) obtaining coordinates for a three-dimensional structure of a Smurf1 protein or a WW-2 motif containing fragment thereof; and b) selecting the agent by performing a rational drug design with the three-dimensional coordinates, wherein said selection is performed in conjunction with computer modeling of a complex between an LMP protein or a fragment thereof and the Smurf1 protein or the fragment thereof.

In another aspect, the invention provides a kit comprising a Smurf1 protein or a fragment thereof capable of ubiquitinating a Smad protein, a source of ubiquitin, a source of ATP, and the Smad protein or a fragment thereof capable of being ubiquitinated by the Smurf1 protein.

In yet another aspect, the invention provides a kit comprising: a first amino acid sequence comprising an amino acid sequence of SEQ. ID NO. 1 ($PPX_1X_2$); and a second amino acid sequence comprising an amino acid sequence at least 70% identical to SEQ. ID. NO. 2 (WW domain of Smurf1) and capable of binding the amino acid sequence of SEQ ID NO 1.

DETAILED DESCRIPTION

Figure 1:
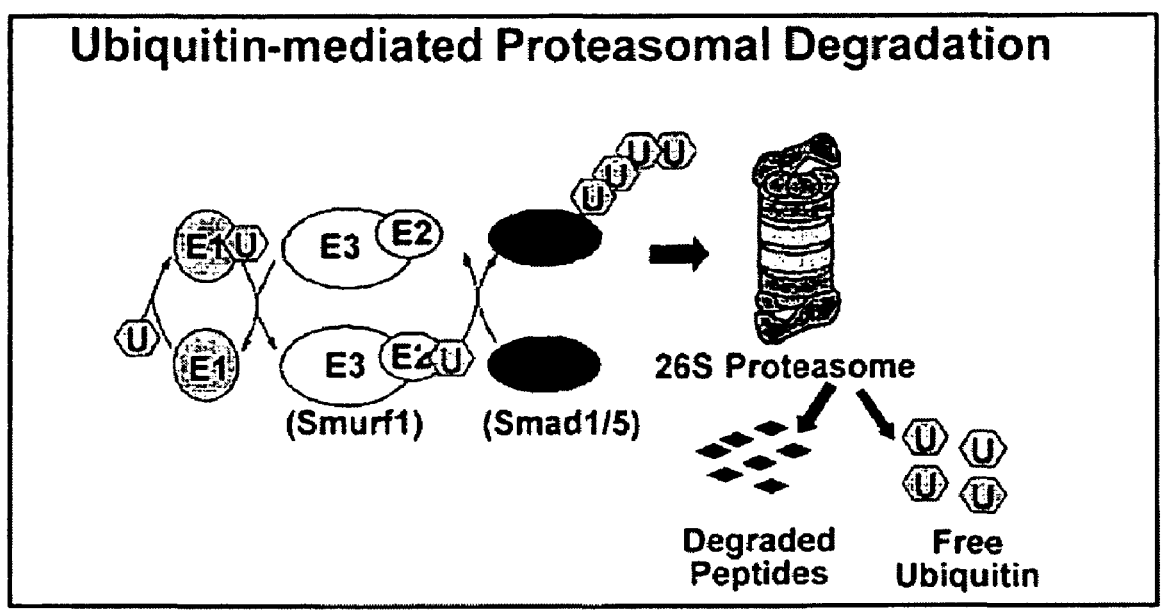
FIG. 1 is a scheme of ubiquitination of the Smad proteins by Smurf1.

The present invention provides an advantageous tool of discovering agents affecting the osteogenic effect of BMPs, including, without limitation, the BMP-2 protein.

As disclosed in the instant disclosure and in application Ser. No. 11/385,612, the LMP proteins, with the exception of LMP-2 (and including LMP-1, LMP-3, and LMP-1t proteins) bind the WW-2 motif of Smurf1 which targets Smad1 and Smad5 proteins for ubiquitination and degradation. Accordingly, binding between the LMP protein and the Smurf1 protein results in decreased ubiquitination of Smads, thus rescuing these Smads for activation via a BMP signaling pathway.

Methods

Accordingly, in a first aspect, the invention comprises a method of identifying an agent affecting a binding between an LMP protein and a Smurf1 protein comprising: providing a first composition comprising: a first amino acid sequence comprising an amino acid sequence of SEQ. ID NO. 1 ($PPX_1X_2$); a second amino acid sequence comprising an amino acid sequence at least 70% identical to SEQ. ID. NO. 2 (WW domain of SMURF1) and capable of binding the amino acid sequence of SEQ ID NO 1; and the agent; and measuring an amount of a complex formed between the first amino acid sequence and the second amino acid sequence in the first composition.

In one embodiment, the first amino acid sequence comprises an amino acid sequence which is capable of binding the WW-2 domain of the Smurf1 protein. Generally, the consensus sequence for a WW-2 binding sequence is PPXY. In the osteogenic region of the LMP proteins, two putative WW-2 sites have been found: SEQ. ID. NO. 3, ADPPRYTFAP and SEQ. ID. NO. 4, GAPPPADSAP. As disclosed previously, it appears that the SEQ. ID. NO. 4 is more crucial than the SEQ. ID. NO. 3. Further, the inventors discovered that a mutation of three prolines in the site B resulted in a loss of any effect of LMP on binding with Smurf1 and Smad ubiquitination. Accordingly, in different embodiments of the invention, SEQ. ID. NO. 1 is PPPA (SEQ. ID. NO. 5) or PPAR (SEQ. ID. NO. 6). In yet another embodiment, SEQ. ID. NO. 1 is the SEQ. ID. NO. 4.

The second amino acid sequence represents a sequence similar to the WW-2 domain of the Smurf1 protein. In different embodiments of the invention, the sequence may be at least 70% identical, or least 75% identical, or least 80% identical, or least 85% identical, or least 90% identical, or least 95% identical, or least 99% identical, or 100% identical to the WW-2 domain of the Smurf1 protein.

The inventors further compared different WW domain sequences in various proteins (SEQ. ID. NO. 2, 7-26). This comparison revealed that amino acids in positions corresponding to positions 3, 4, 7, 8, 18, 19, 20, 21, 22, 23, 25, 27, 31, 32, and 33 of SEQ. ID. NO. 2 are conserved or have very little variation among different WW domains. Thus, in one embodiment, the second sequence includes leucine at a position corresponding to positions 3, of SEQ. ID. NO. 2; proline at a position corresponding to position 4 of SEQ. ID. NO. 2; tryptophan at a position corresponding to position 7 of SEQ. ID. NO. 2; glutamic acid at a position corresponding to position 8 of SEQ. ID. NO. 2; phenylalanine or isoleucine at a position corresponding to position 18 of SEQ. ID. NO. 2; phenylalanine or isoleucine at a position corresponding to position 19 of SEQ. ID. NO. 2; valine or isoleucine at a position corresponding to position 20 of SEQ. ID. NO. 2; asparagine or aspartic acid at a position corresponding to position 21 of SEQ. ID. NO. 2; histidine at a position corresponding to position 22 of SEQ. ID. NO. 2; asparagine, valine, proline or serine at a position corresponding to position 23 of SEQ. ID. NO. 2; arginine or lysine at a position corresponding to position 25 of SEQ. ID. NO. 2; serine or threonine at a position corresponding to position 27 of SEQ. ID. NO. 2; aspartic acid at a position corresponding to position 31 of SEQ. ID. NO. 2; proline at a position corresponding to position 32 of SEQ. ID. NO. 2; and arginine at a position corresponding to position 33 of SEQ. ID. NO. 2.

The inventors further analyzed SEQ. ID. NO. 2 to determine which amino acid residues are likely to participate in interacting with target motif of the WW-2 domain. The analysis revealed that arginine at a position corresponding to position 10 of SEQ. ID. NO. 2; tyrosine at a position corresponding to position 18 of SEQ. ID. NO. 2; arginine at a position corresponding to position 25 of SEQ. ID. NO. 2; threonine at a position corresponding to position 27 of SEQ. ID. NO. 2; and glutamine at a position corresponding to position 28 of SEQ. ID. NO. 2 are the likely candidates for the amino acid residues involved in interaction with the WW-2 domain. Accordingly, in another embodiment, the second amino acid sequence comprises arginine at a position corresponding to position 10 of SEQ. ID. NO. 2; tyrosine at a position corresponding to position 18 of SEQ. ID. NO. 2; arginine at a position corresponding to position 25 of SEQ. ID. NO. 2; threonine at a position corresponding to position 27 of SEQ. ID. NO. 2; and glutamine at a position corresponding to position 28 of SEQ. ID. NO. 2.

In a more preferred embodiments, both analyses described above are taken into consideration. Accordingly, the second amino acid sequence comprises leucine at a position corresponding to positions 3 of SEQ. ID. NO. 2; proline at a position corresponding to position 4 of SEQ. ID. NO. 2; tryptophan at a position corresponding to position 7 of SEQ. ID. NO. 2; glutamic acid at a position corresponding to position 8 of SEQ. ID. NO. 2; phenylalanine or isoleucine at a position corresponding to position 18 of SEQ. ID. NO. 2; phenylalanine or isoleucine at a position corresponding to position 19 of SEQ. ID. NO. 2; valine or isoleucine at a position corresponding to position 20 of SEQ. ID. NO. 2; asparagine or aspartic acid at a position corresponding to position 21 of SEQ. ID. NO. 2; histidine at a position corresponding to position 22 of SEQ. ID. NO. 2; asparagine, valine, proline or serine at a position corresponding to position 23 of SEQ. ID. NO. 2; arginine or lysine at a position corresponding to position 25 of SEQ. ID. NO. 2; serine or threonine at a position corresponding to position 27 of SEQ. ID. NO. 2; aspartic acid at a position corresponding to position 31 of SEQ. ID. NO. 2; proline at a position corresponding to position 32 of SEQ. ID. NO. 2; and arginine at a position corresponding to position 33 of SEQ. ID. NO. 2, as well as arginine at a position corresponding to position 10 of SEQ. ID. NO. 2; tyrosine at a position corresponding to position 18 of SEQ. ID. NO. 2; and glutamine at a position corresponding to position 28 of SEQ. ID. NO. 2. In yet another embodiment, the second amino acid sequence comprises a full length Smurf1 protein. In different embodiment, the Smurf1 protein is selected from Smurf1 proteins of different species, suitable non-limiting examples including SEQ. ID. NO. 27 (human Smurf1 protein), SEQ. ID. NO. 28 (*Xenopus* Smurf1 protein), SEQ. ID. NO. 29 (mouse Smurf1 protein), and SEQ. ID. NO. 30 (chimpanzee Smurf1 protein).

Thus, the person of the ordinary skill in the art, may combine the agent, the first amino acid sequence and the second amino acid sequence, in accordance with the embodiments described above, and measure an amount of the complex between the first and the second amino acid sequences.

As a negative control, the person of the ordinary skill in the art may measure an amount of a complex between a third amino acid sequence and a fourth amino acid sequence in a second composition, wherein the second composition contains another, smaller amount of the agent, or, more preferably, does not contain the agent at all. A person of the ordinary skill in the art possesses a sufficient expertise to realize that the first amino acid sequence should be functionally equivalent to the first amino acid sequence and the fourth amino acid sequence should be functionally equivalent to the second amino acid sequence. Preferably, the third amino acid sequence is identical to the first amino acid sequence and the fourth amino acid sequence is identical to the second amino acid sequence. This requirement, however, is not absolute: for example, the second and the fourth sequences may differ in length (e.g., by 5 amino acid residues or fewer) or in composition. For example, amino acids which are not conserved between different WW-2 domains may be different, but preferably, of the same class (e.g. hydrophobic, non-polar, polar, positively-charged, or negatively-charged).

Thus, after comparing the amounts of the complexes in the first and in the second compositions, the person of the ordinary skill in the art will be able to conclude whether the agent induces or inhibits the formation of such complex between the first and the second amino acid sequences.

Upon comparing the amounts of the complexes in the first and second compositions, the person may properly conclude that the increased amount of the complex in the first composition indicates that the agent induces binding between the amino acid sequence of SEQ. ID NO. 1 and the amino acid sequence of SEQ. ID. NO. 2; and the decreased amount of the complex in the first composition indicates that the agent inhibits binding between the amino acid sequence of SEQ. ID NO. 1 and the amino acid sequence of SEQ. ID. NO. 2.

Further, the person of the ordinary skill in the art may properly conclude that the increased amount of the complex in the first composition indicates that the agent inhibits ubiquitination of a Smad protein by Smurf1; and the decreased amount of the complex in the first composition indicates that the agent induces ubiquitination of a Smad protein by Smurf1. In different embodiments of the invention, the Smad protein includes Smad1, Smad5, and Smad6 proteins.

Following the model described herein and in the U.S. application Ser. No. 11/385,612, the person of the ordinary skill in the art may also properly conclude that the increased amount of the complex in the first composition indicates that the agent induces an osteogenic effect of an LMP protein or a fragment thereof; and the decreased amount of the complex in the first composition indicates that the agent inhibits an osteogenic effect of an LMP protein or a fragment thereof.

And yet further, the person of the ordinary skill in the art may also properly conclude that the increased amount of the complex in the first composition indicates that the agent induces an osteogenic effect of a BMP protein or a fragment thereof; and the decreased amount of the complex in the first composition indicates that the agent inhibits an osteogenic effect of the BMP protein or a fragment thereof. In one embodiment of the invention, the BMP-2 protein or a functionally equivalent fragment thereof are suitable non-limiting examples of the BMP protein.

In a second aspect, the invention provides a method of identifying an agent affecting ubiquitination of a Smad protein by Smurf1 comprising: providing a first composition comprising a first amino acid sequence comprising an amino acid sequence of SEQ. ID NO. 1 ($PPX_1X_2$); a second amino acid sequence comprising an amino acid sequence at least 70% identical to SEQ. ID. NO. 2 (WW domain of Smurf1), said second amino acid sequence capable of binding the amino acid sequence of SEQ ID NO 1 and of ubiquitinating the Smad protein; the Smad protein or a fragment thereof capable of being ubiquitinated by Smurf1; a source of ubiquitin; a source of ATP; the agent; and measuring an amount of a ubiquitinated Smad protein or the ubiquitinated fragment thereof in the first composition. The method further comprises comparing the amount of the complex in the first composition with an amount of a complex formed between a third amino acid sequence and a fourth amino acid sequence in a second composition, wherein said second composition comprises a source of ubiquitin and a source of ATP; said second composition includes a different, smaller amount of the agent (or, preferably, does not include the agent); the third amino acid sequence comprises an amino acid sequence of SEQ. ID NO. 1; and the fourth amino acid sequence comprises an amino acid sequence at least 70% identical to SEQ. ID. NO. 2, said second amino acid sequence capable of binding the amino acid sequence of SEQ. ID. NO. 1 and of ubiquitinating the Smad protein of the fragment thereof.

The requirements for the first, the second, the third, and the fourth amino acid sequences have been described with regard to the previous aspect of the invention. The same requirements apply for the instant aspect of the invention. However, there is an additional requirement for the second (and, respectively, the fourth) amino acid sequence: the second amino acid sequence should be able to ubiquitinate the Smad protein, which, in different embodiments of the invention includes Smad1, Smad5, and Smad6 proteins, as well as the fragments thereof capable of being ubiquitinated by Smurf1.

At the very minimum, the Smad proteins or the fragments thereof should include the potential WW binding sites (PPXY, as described above). These sequences have been described in respective amino acid sequences of the Smad1 protein and the Smad5 proteins and include, for example, amino acids 222-226 of the Smad5 protein (full sequence of the human Smad5 protein is shown in SEQ. ID. NO. 31) and amino acids 223-227 of the Smad1 protein (full sequence of the human Smad1 protein is shown in SEQ. ID. NO. 32). Thus, in different embodiments, the fragments of the Smad1 protein and the Smad5 protein comprise, respectively, amino acid sequences of SEQ. ID. NO. 33 and SEQ. ID. NO. 34).

The Smad protein or the fragment thereof should preferably be identical. Even though the complete sequence identity is preferred, it is not strictly required. For example, amino acid sequences of different lengths can be used, as long as these sequences display the same affinity and avidity of binding to the Smurf1 protein and the same ubiquitination ratios. Further, as long as these sequences display the same affinity and avidity of binding to the Smurf1 protein and the same ubiquitination ratios, these amino acid sequences may have different amino acid composition (e.g., substitutions, preferably, conservative substitutions).

Further, the first and the second compositions should comprise a source of ubiquitin, and a source of ATP. In a cell, ubiquitin, upon activation and conjugation, is present in a complex with E2 ligase (ubiquitin-conjugating enzyme), which binds the Smurf1 protein. Thus, in the method, the ubiquitin may be provided in a complex with the E-2 ligase, or the E-2 ligase and the ubiquitin may be provided separately, but in the latter embodiment, the conditions of the first and the second compositions should be such that the complex between the ubiquitin and the E-2 ligase could be formed. In one example, the composition would comprise a free ubiquitin from a recombinant source, the E-2 ligase, the E-1 ligase (ubiquitin-activating enzyme), and the source of ATP.

Following the model discovered by the inventors, a person of the ordinary skill in the art may properly conclude that an increased amount of the ubiquitinated Smad protein in the first composition indicates that the agent induces ubiquitination of the Smad protein by Smurf1; and a decreased amount of the ubiquitinated Smad protein in the first composition indicates that the agent inhibits ubiquitination of the Smad protein by Smurf1.

Further, the person of the ordinary skill in the art may properly conclude that an increased amount of the ubiquitinated Smad protein in the first composition indicates that the agent inhibits an osteogenic effect of a BMP protein; and a decreased amount of the ubiquitinated Smad protein in the first composition indicates that the agent induces an osteogenic effect of the BMP protein. The BMP-2 protein and a functionally equivalent fragment thereof represent suitable non-limiting examples of the BMP protein, which may be used in different embodiment of the invention.

In a third aspect, the invention provides method of identifying an agent affecting ubiquitination of a Smad protein by a Smurf1 protein comprising: providing a first composition comprising: the Smurf1 protein or a fragment thereof capable of ubiquitinating the Smad protein; a source of ubiquitin; a source of ATP, and the Smad protein or a fragment thereof capable of being ubiquitinated by the Smurf1 protein; the agent; and measuring an amount of ubiquitinated Smad protein or the fragment thereof in the first composition.

The method further comprises comparing the amount of the ubiquitinated Smad protein or the fragment thereof in the first composition with an amount of ubiquitinated Smad protein or a fragment thereof in a second composition, wherein said second composition includes a smaller amount of the agent (or preferably does not include the agent at all); and said second composition comprises the Smurf1 protein or a fragment thereof capable of ubiquitinating the Smad protein; a source of ubiquitin; a source of ATP; the Smad protein or a fragment thereof capable of being ubiquitinated by the Smurf1 protein.

A person of the ordinary skill in the art will appreciate that the description of the amino acid sequence comprising the Smurf1 protein or a fragment thereof capable of ubiquitinating the Smad protein has been described with regard to the second aspect of invention as the second or the fourth sequences. Further, suitable Smad protein or the fragments thereof, as well as ubiquitin sources have also been described with regard to the second aspect of the instant invention.

Following the model described by the inventors, the person of the ordinary skill in the art may properly conclude that an increased amount of the ubiquitinated Smad protein indicates that the agent increases ubiquitination of the Smad protein by Smurf1; and a decreased amount of the ubiquitinated Smad protein indicates that the agent decreases ubiquitination of the Smad protein by Smurf1.

Further, the person of the ordinary skill in the art may also conclude that an increased amount of the ubiquitinated Smad protein indicates that the agent inhibits an osteogenic effect of a BMP protein; and a decreased amount of the ubiquitinated Smad protein indicates that the agent induces an osteogenic effect of the BMP protein.

A person of the ordinary skill in the art will appreciate that the amino acid sequences, proteins and protein fragments described in the instant disclosure (including, without limitation, the first amino acid sequence, the second amino acid sequence, the third amino acid sequence, the fourth amino acid sequence, or the Smad protein or the fragment thereof) may be obtained by multiple methods. For example, they may be ordered from a manufacturer, such as, for example, New England Peptide, Inc. (Gardner, Mass.).

In another embodiment, the amino acid sequences of the instant invention can be synthesized by standard solid peptide synthesis (Barany, G. and Merrifield, R. B., The Peptides 2:1 284, Gross, E. and Meienhofer, J., Eds., Academic Press, New York) using tert-butyloxycarbonyl amino acids and phenylacetamidomethyl resins (Mitchell, A. R. et al., *J. Org. Chem.* 43:2845 2852 (1978)) or 9-fluorenylmethyloxycarbonyl amino acids on a polyamide support (Dryland, A. and Sheppard, R. C., J. Chem. So. Perkin Trans. I, 125 137 (1986)). Alternatively, synthetic peptides can be prepared by pepscan synthesis (Geysen, H. M. et al., *J. Immunol. Methods* 03:259 (1987); *Proc. Natl. Acad. Sci. USA* 81:3998 (1984)), Cambridge Research Biochemicals, Cambridge, U.K. or by standard liquid phase peptide synthesis.

In another embodiment, the amino acid sequences may be purified from a cellular source. The suitable sources include cells which natively express peptides containing those sequences as well as artificial expression system. The former include, without limitation, cultured osteoblasts and cultured intervertebral disc cells. The purification techniques are well known in the art. One suitable method of purification is affinity chromatography. Essentially, in this technique, the cell extract is passed through a column impregnated with antibodies specifically recognizing the amino acid sequence of interest. With regard to the instant disclosure, the amino acid sequence of interest includes, without limitation, Smad proteins and Smurf1 protein.

In yet another embodiment, the amino acid sequences of the instant invention can be recombinantly produced. For example, the mRNA and cDNA sequences of the LMP protein (LMP-1 cDNA is recited in SEQ. ID. NO. 35, LMP-1s cDNA is recited in SEQ. ID. NO. 36), the Smad proteins (Smad1 cDNA SEQ. ID. NO. 37, Smad5 cDNA SEQ. ID. NO. 38) and the Smurf protein (Smurf1 cDNA SEQ. ID. NO. 39) are well known in the art. Information regarding these and other amino acid and nucleic acid sequences which may be useful for certain embodiments of the instant invention (e.g., the amino acid and nucleic acid sequences for E-1 and E-2 ligases) are available, for example, from Genbank. Thus, the primers may be designed to multiply the nucleic acid sequence encoding the amino acid sequence of interest by PCR (if the template is cDNA) or RT-PCR (if the template is mRNA).

This nucleic acid sequence encoding the amino acid sequence of interest may be subcloned into a vector by methods well known in the art utilizing endonuclease and ligase properties. The vector may be either plasmid or viral vector. Suitable plasmid vectors include, without limitation, pUC18 and pUC 19. Suitable viral vectors include adenoviral vectors, adeno-associated vectors and baculoviral vectors. Additional examples of vectors are listed in catalogs of different manufacturers, including, without limitation, Promega Corp. (Madison, Wis.), incorporated herein by reference in its entirety.

Further, the vector may contain a promoter which directs the expression of the amino acid sequence of interest from the nucleic acid sequence. Suitable promoters include, without limitation, CMV, RSV, and TK. The vector containing the nucleic acid sequence encoding the amino acid sequence of interest is later introduced to host cells.

The choice of the host cell system depends largely on the type of the vector and the type of the promoter. In general, the host cells include, without limitations, prokaryotic, yeast, insect, and mammalian cells. Essentially, the host cells should be selected based on the nature of the vector.

Further, depending on the type of the host cell, the codons of the nucleic acid sequences encoding the amino acid sequences of the instant invention can be selected for optimal expression in prokaryotic or eukaryotic systems. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

The amino acid sequences used in the kits and the methods of the instant invention can be purified or partially purified from cells comprising the vector, comprising the nucleic acid sequence encoding the amino acid sequence of interest, using known purification processes such as gel filtration and ion exchange chromatography. Purification may also include affinity chromatography with agents known to bind the respective amino acid sequences.

Further, the amino acid sequences of interest may be tagged, as described in more details below. In one non-limiting example, the recombinant nucleic acid sequences are fused with a nucleic acid sequence encoding glutathione-S-transferase (GST). The GST-tag is often used to separate and purify proteins that contain the GST-fusion. GST-fusion proteins can be produced in *E. coli*, as recombinant proteins. The GST part binds its substrate, glutathion. Sepharose beads can be coated with glutathion, and such glutathion-sepharose beads bind GST-proteins. These beads are then washed, to remove contaminating bacterial proteins. Adding free glutathion to beads that bind purified GST-proteins will release the GST-protein in solution.

Once purified, the cleavage of the amino acid sequences of the instant invention into fragments of amino acid residues can be achieved using proteolytic enzymes such as thrombin or clostridiopeptidase B (clostripain). The exact time required for proteolysis varies with each preparation and markedly depends upon the batch of clostripain used. Therefore, the optimum time for a single cleavage must be determined for each combination of clostripain batch and the amino acid sequence used (e.g., the first amino acid sequence, the second amino acid sequence, the third amino acid sequence, the fourth amino acid sequence, the Smad protein or the fragment thereof, or the ubiquitin). The protein fragments resulting from either thrombin or clostripain proteolysis may be further cleaved by digestion with trypsin, which cleaves on the carboxy terminus of lysine or arginine residues.

The peptides derived from proteolytic digestion may be identified using the Edman degradation method of protein sequencing. In addition, sequence analysis of the recombinant NS1A protein may be accelerated by using an automated liquid phase amino acid sequenator, thereby allowing for the analysis of picomolar quantities of the recombinant proteins containing up to 50 amino acid residues in length.

A non-limiting example of one suitable source of ATP is ATP itself, which can be ordered, for example, from Sigma-Aldrich Co. (St. Louis, Mo.). Further, an ATP-generating system may be used, for example, as described in Adeli et al., *J. Biol. Chem.* 272(8): 5031-5039 (1997). In that reference, the ATP-generating system was created by combining 5 parts of 40 mM ATP with 5 parts of 200 mM creatine phosphate and 1 part of rabbit muscle creatine phosphokinase (100 units/ml).

Detection Assays

The detection assays described herein are applicable to all aspects of the invention, including both methods described above and the kits described below.

The amounts of the complex in the first composition or in the second composition, or the amounts of the ubiquitinated Smad proteins or the fragments thereof can be readily determined by any number of assays widely known in the art, such as for example, a competition or sandwich ELISA, a radioimmunoassay, a dot blot assay, a fluorescence polarization assay, a scintillation proximity assay, a homogeneous time resolved fluorescence assay, a resonant mirror biosensor analysis, and a surface plasmon resonance analysis.

Generally, these methods require that at least one compound of the complex or the composition amount of which is to be measured should be directly or indirectly labeled with a detection means, as described in details below.

Suitable detection means are widely known in the art and include various enzymes, prosthetic groups, tags, fluorescent materials, luminescent materials, magnetic agents and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; examples of a luminescent material include luminol luciferin, pyrogallol, or isoluminol; an example of a magnetic agent includes gadolinium.

For example, some technical problems for the adequate analysis of the expression of cloned cDNA are the lack of functional assays and/or specific antibodies (Ab) to the proteins produced. To overcome this difficulty fusion proteins where a known peptide is fused to the expression product have been described. In addition to the Flag-Tag, His-tag and GST-tag are widely used.

GST stands for glutathione-S-transferase, commonly used to create fusion proteins. The tag has the size of 220 amino acids, which is compared to other tags, like the myc-, or the FLAG-tag quite large. It is fused to the N-terminus of a protein.

A polyhistidine-tag is an amino acid motif in proteins that consists of at least six histidine (His) residues, often at the N— or C-terminus of the protein. It is also known as hexa histidine-tag, 6×His-tag, and by the trademarked name His-tag® (registered by EMD Biosciences). The tag was invented by Roche and its vectors and NTA (nitrilotriacetic acid) protein purification kits are distributed by Qiagen. Suitable tag sequences are available for free commercial use; for example, MK(HQ)6 may be used for enhanced expression in *E. coli* and tag removal. The total number of histidine residues may vary in the tag.

The His-tag may also be followed by a suitable amino acid sequence that facilitates a removal of the polyhistidine-tag using endoproteases. This extra sequence is not necessary if exopeptidases are used to remove N-terminal His-tags (e.g., Qiagen TAGZyme). Furthermore, exopeptidase cleavage may solve the unspecific cleavage observed when using endoprotease-based tag removal.

Further, detection means may comprise other labels including, without limitation, fluorescent molecule such as, for example, Fluoroscein, Rhodamine, AMC, Biotin, which can be ordered from New England Peptides, Inc.

Further, the amino acid sequences may comprise radioactive labels, including, without limitation $^3$H, $^{14}$C, $^{15}$N, $^{18}$O, $^{35}$S, and $^{32}$P. These radiolabels are usually incorporated within different amino acids and then these amino acids may be used during the synthesis of the amino acid sequences of interest. The amino acids labeled with the radioactive labels are available from different manufacturers, including, without limitation, Sigma Corp (St Louis, Mo.).

In yet another embodiment, the detection means may comprise antibodies to any of the compounds of the first or the second compositions, as described above, or the kits, as described below, including, without limitation, the first amino acid sequence, the second amino acid sequence, the third amino acid sequence, the fourth amino acid sequence, the Smad protein or the fragment thereof, the ubiquitin, and the ubiquitinated Smad protein or the fragment thereof.

The essays suitable for the kits and methods of the instant invention may be performed in cell systems or cell-free systems. Thus, the first and the second compositions, as described in the first, second, and third aspects of the invention may be cell-free compositions or may comprise cells.

Different cells are suitable for the kits and methods of the instant invention. Suitable cells include, without limitation, *E. coli* cells transformed with the plasmids comprising the nucleic acid sequences encoding the amino acid sequences used for the kits and methods of the instant invention, rat calvarian cultures, or $C_2C_{12}$ cells. The vectors comprising the nucleic acid sequences encoding the amino acid sequences of the instant invention (including the Smad protein or the fragment thereof and the components of the source of ubiquitin) may be introduced into the cells by methods well known in the art. The vectors may be plasmid or viral vectors as described above.

In another embodiment, the first and the second compositions are cell-free systems. It is preferable that the composition mimics the conditions in vivo (e.g., ionic strength and pH), where the respective reaction (e.g., the formation of the complex between the first and the second amino acid sequences) takes place.

If the chosen embodiment comprises a cell-free composition, one component of the composition may be immobilized on a substrate, e.g., bound to sepharose beads. For example, if the amount of the complex between the first and the second amino acid sequence is measured, one amino acid sequence (e.g., the first amino acid sequence) may be immobilized.

Further, the other component may be labeled with the detection means as described in the instant application. Thus, the measurement of the amount of the detection means bound to the substrate will provide a measurement of the complex between the first and the second amino acid sequences.

By the same token, in the kits and methods which measure the amount of the ubiquitinated Smad protein or the fragment thereof, a person of the ordinary skill in the art may select to bind the source of the ubiquitin to a substrate, and to measure the amount of the Smad protein or the fragment thereof labeled with the detection means and bound to the substrate. In another embodiment, the Smad protein or the fragment thereof is immobilized on the substrate and the ubiquitin is labeled with the detection means. In this embodiment, the measurement of the amount of the ubiquitin bound to the substrate (via the Smad protein or the fragment thereof) will provide a person of the ordinary skill in the art with the inference about the amount of the ubiquitinated Smad protein or the fragment thereof.

In yet another embodiment, both free-flowing member (e.g., the first amino acid sequence) and the immobilized member (e.g., the second amino acid sequence) may be labeled with the detection means. For example, different fluorescent means may be used to label the first amino acid sequence and the second amino acid sequence. Co-localization of these labels indicates that the first amino acid sequence is bound to the second amino acid sequence and not non-specifically bound to the substrate.

Generally, in one embodiment, the member of the complex (e.g., the first amino acid sequence or the second amino acid sequence, or the Smad protein or the fragment thereof or the ubiquitin is directly labeled with the detection means and may be detected directly. In another embodiment, of these compounds is labeled. Instead, an antibody or other molecule that can bind these compounds is labeled. For example, and without any limitations, in one embodiment, the kit is prepared for a method comprising the measurement of the complex between the first and the second amino acid sequences. Further, let's assume that in this embodiment the first amino acid sequence is immobilized. The second amino acid sequence may comprise a detection means, such as, for example a tag, e.g., a His tag. The antibodies to the His tag are well known and commercially available. These antibodies may comprise another detection means, such as for example, a fluorescent label or a radioactive label. The amount of the complex between the first and the second amino acid sequences in the biological sample can be detected by detecting the presence of the labeled antibody. Other molecules that can bind to antibodies include, without limitation, Protein A and Protein G, both of which are available commercially, for example, from Pierce Chemical Co. (Rockford, Ill.).

The antibodies to the amino acid sequences of the instant invention can be produced by methods well known to those skilled in the art. For example, monoclonal antibodies can be produced by generation of hybridomas in accordance with known methods. Hybridomas formed in this manner are then screened using standard methods, such as ELISA, to identify one or more hybridomas that produce an antibody that specifically binds to an epitope contained within the respective amino acid sequence of the instant invention.

As an alternative to preparing monoclonal antibody-secreting hybridomas, the monoclonal antibodies to the amino acid sequences of the instant invention may be identified and isolated by screening a recombinant combinatorial immunoglobulin library (e.g., an antibody phage display library) to thereby isolate immunoglobulin library members that bind to the amino acid sequences of the instant invention. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with the respective amino acid sequence of the instant invention. The antibody titer in the immunized subject may be monitored over time by standard techniques, such as with ELISA, using immobilized marker protein. If desired, the antibody molecules directed against the respective amino acid sequences of the instant invention may be isolated from the subject or culture media and further purified by well-known techniques, such as protein A chromatography, to obtain an IgG fraction, or by affinity chromatography.

Fragments of antibodies to the amino acid sequences of the instant invention may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to the amino acid sequences of the instant invention, comprising both human and nonhuman portions, may be produced using standard recombinant DNA techniques.

Humanized forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. Thus, essentially, humanizing involves assembly of hypervariable regions of a non-human antibody and conserved regions of human antibodies.

The humanization techniques are well known in the art. Further, some humanization protocols are commercially available, for example, from Diversa Corp (San Diego, Calif.). Humanized antibodies to the amino acid sequence of the instant invention may also be produced using transgenic mice that are incapable of expressing endogenous immunoglobulin heavy and light chain genes, but which can express human heavy and light chain genes. Kits In a fourth aspect, the invention provides a kit comprising: a first amino acid sequence comprising an amino acid sequence of SEQ. ID NO. 1; and a second amino acid sequence comprising an amino acid sequence at least 70% identical to SEQ. ID. NO. 2 and capable of binding the amino acid sequence of SEQ ID NO 1. These amino acid sequences have been described with regard to the first aspect of the invention.

The kit may further comprise the Smad protein or the fragment thereof capable of being ubiquitinated by the Smurf1 protein, a source of ubiquitin, and a source of ATP. The suitable Smad proteins (including the fragments thereof), the sources of ubiquitin, and the sources of ATP have also been described in the instant application with regards to the previous aspects of the instant invention.

The kit may further comprise detection means. The precise nature of the detection means ultimately depends on the method by which the amount of the complex between the first and the second amino acid sequence is measured. The detection means may be included independently and/or incorporated within the first and the second amino acid sequences.

The suitable non-limiting examples of the detection means are disclosed in details in the section Assays of this application. These detection means are fully applicable to all embodiments of the kits discussed herein.

In yet another embodiment, the kit comprises a set of instructions for efficient and safe use of the kit. A person skilled in the art will undoubtedly appreciate that the set of instruction may be provided in any medium, including, without limitations, printed, audio and video recorded, and electronic.

In a fifth aspect, the invention provides a kit for determining whether an agent induces or inhibits ubiquitination of the Smad protein or the fragment thereof by the Smurf1 protein, comprising a Smurf1 protein or a fragment thereof capable of ubiquitinating a Smad protein; a source of ubiquitin; a source of ATP; and the Smad protein or a fragment thereof capable of being ubiquitinated by the Smurf1 protein. The components of the kit according to this fifth aspect of the invention, as well as the methods of making and using those components within a kit, including, without limitations, the kit of the instant aspect of the invention, are described in this application with regards to the previous aspects of the instant invention.

Computer-Aided Method of Identifying Agents of Interest.

In the sixth broad aspect, the invention provides A method of identifying an agent affecting a binding between an LMP protein and a Smurf1 protein comprising: a) obtaining coordinates for a three-dimensional structure of a Smurf1 protein or a WW-2 motif containing fragment thereof; b) selecting the agent by performing a rational drug design with the three-dimensional coordinates, wherein said selecting is performed in conjunction with computer modeling of a complex between an LMP protein or a fragment thereof and the Smurf1 protein or the fragment thereof. The 3-dimensional coordinates of the Smurf1 protein or the WW-2 motif containing fragment thereof may be obtained by multiple methods. For example, these coordinates may be obtained experimentally, such as, for example, by X-ray crystallography. In another embodiment, computer modeling may be used to obtain the three-dimensional coordinates of the Smurf1 protein or the WW-2 motif containing fragment thereof. For example, these coordinates may be modeled by using MODELLER as well as SWISS_MODEL software packages (Ascelrys, Inc. San Diego, Calif.).

Further, grid docking (AFFINITY) procedure may be employed for the interaction between the agent and the Smurf1 or the WW-2 motif containing fragment thereof.

A person of the ordinary skill in the art will appreciate that the computer-aided drug design may increase the efficiency of the methods and kits of the previous aspects of the invention. Accordingly, in one embodiment, the computer-aided drug design method is used in conjunction with any of the methods and kits described in the first through the fifth aspects of the invention. For example, the potential compounds may first be tested via a computer aided drug design method of the instant aspect of the invention, as the initial selection/identification round. After this initial round of selection/identification, the leading candidates may be tested according to any or all methods, optionally, using the appropriate kits of the instant invention.

The invention will be further described in the following non-limiting examples.

EXAMPLES

Example 1

Identification of WW-Domain Interacting Motifs in LMP-1

To corroborate experimental data on bone forming region of LMP-1 sequence with computational motif analysis, we used iSPOT, a web tool useful to infer the recognition specificity of protein module families such as PDZ, SH3 and WW domains. For each of the given family of protein domains, iSPOT evaluates the probability of interaction between a query domain of the specified families and an input protein/peptide sequence. Using the iSPOT server we have analyzed the LMP-1 sequence to identify potential WW domain binding motifs. The iSPOT identified two motifs with binding affinity for WW domains within the 45 amino acid osteogenic region of LMP-1. The motifs, SEQ. ID. NO. 40, ADPPRYTF (0.79) and SEQ. ID. NO. 41, GAPPPADSA (0.61) are predicted to be potential binding sequences with binding affinity for the Smurf1 WW2 domain.

Example 2

Comparison of Smurf1 WW2 Domain with Known WW-Domain Structures

Figure 2:
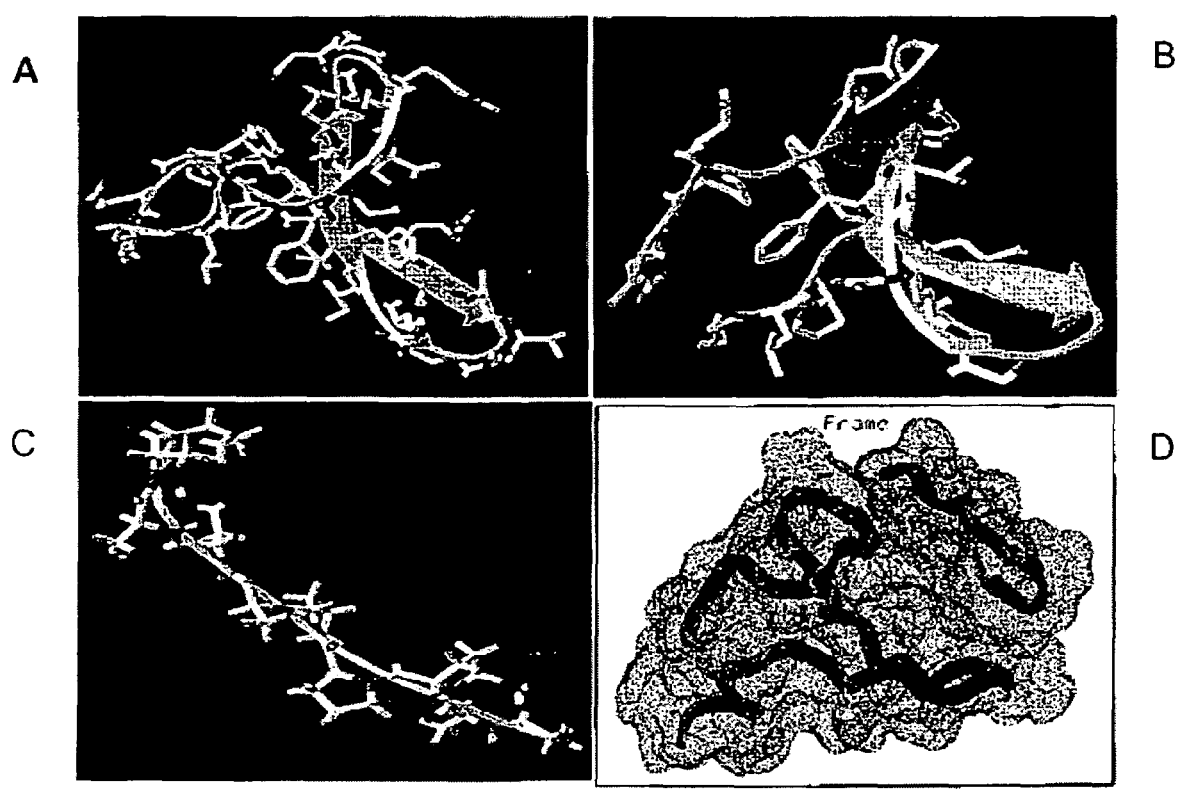
FIG. 2 illustrates predicted three-dimentional structures for the WW-2 domain of Smurf1 (FIG. 2A, FIG. 2B), a model of the peptide motif structures of WW domain interacting site B of LMP-1 (FIG. 2C), and a model of binding between WW-2 domain of Smurf1 and the WW domain interacting site B of LMP-1 (FIG. 2D).

In order to obtain homologous structures of Smurf1-WW2 sequences we have BLASTed this sequence against the protein data bank (PDB) sequences. It can be seen from Table 1 that there are six structures in PDB with significant homology scores. BLAST expectation (E value) scores obtained are less than $4e^{-5}$. The bit scores obtained are greater than 40 with the sequence identity greater than 45% for Smurf1-WW2 domain. The sequences of structures 1TK7:A and 1I5H:W showed expectation values (E Value) $2e^{-9}$ and $2e^{-8}$, and bit scores of 55 and 52, respectively (Table I). We have therefore used these two structures as basis to model the structure of Smurf1-WW2 domain (FIG. 2A & 2B).

TABLE I

Comparison of Smurf1 WW2 domain with known WW-domain structures available in the PDB. The Blast scores are given for each of the sequence compared to the Smurf1-WW2 domain sequence.

| PDB-ID | Seq. ID. | Pos | WW2-domain of SMURF1 homologues | E-Value | % | Bit |
|---|---|---|---|---|---|---|
| Smurf1WW2 | 2 | | GPLPPGWEVRSTVSGRIYFVDHNNRTTQFTDPRL | | | |
| 1TK7:A | 13 | 55 | GPLPPGWEIRYTAAGERFFVDHNTRRTTFEDPR- | 2e-09 | 66% | 55 |
| 1I5H:W | 42 | 10 | GPLPPGWEERTHTDGRVFFINHNIKKTQWEDPRM | 2e-08 | 55% | 52 |

TABLE I-continued

Comparison of Smurf1 WW2 domain with known WW-domain structures available in the PDB. The Blast scores are given for each of the sequence compared to the Smurf1-WW2 domain sequence.

| PDB-ID | Seq. ID. | Pos | WW2-domain of SMURF1 homologues | E-Value | % | Bit |
|---|---|---|---|---|---|---|
| 1EOM:A | 43 | 4 | --LPPGWDEYKTHNGKTYYYNHNTKTSTWTDPRM | 1e-05 | 46% | 43 |
| 1K9R:A | 44 | 8 | -PLPAGWEMAKTSSGQRYFLNHIDQTTTWQDPR- | 1e-05 | 53% | 43 |
| 1JMQ:A | 45 | 8 | -PLPAGWEMAKTSSGQRYFKNHIDQTTTWQDPR- | 3e-05 | 53% | 42 |
| 1K5R:A | 46 | 8 | -PLPAGWEMAKTSXGQRYFLNHIDQTTTWQDPR- | 4e-05 | 50% | 41 |

Example 3

Identification of Conserved Amino Acids in the WW2 Domain Sequences

In order to see conservation profile of amino acid residues in WW2 domain we have multi-aligned all the homologous sequences and computed the conservation index for each amino acid. Table II gives multiple sequence alignment of twenty homologous sequences of WW2 domain region consisting of 35 residues from the NCBI non-redundant (NR) sequence database. All these domains have been proposed to play important role in target protein interactions. The conservation index of each of amino acid is given the Table II. The amino acid residues with conservation index greater than 0.85 (marked + or *) are indicative of playing significant role in maintaining the domain structure.

TABLE 2

Conservation of amino acids within WW-2 domains.

| Pos | N-terminal end (up) | | | | | | | | | | | | | | | | | | | | Index |
|---|---|---|---|---|---|---|---|---|---|---|---|---|---|---|---|---|---|---|---|---|---|
| 1 | G | G | G | G | G | G | G | G | G | - | G | G | G | G | G | G | G | G | G | G | 1.00* |
| 2 | P | P | P | P | P | P | P | P | P | - | P | A | P | P | P | P | P | S | P | P | 0.88+ |
| 3 | L | L | L | L | L | L | L | L | L | L | L | L | L | L | L | L | L | L | L | L | 1.00* |
| 4 | P | P | P | P | P | P | P | P | P | P | P | P | P | P | P | P | P | P | P | P | 1.00* |
| 5 | P | P | P | P | P | P | E | P | H | P | E | P | S | P | E | H | A | P | A | P | S 0.58 |
| 6 | G | G | G | G | G | G | G | G | G | G | G | G | G | N | G | G | K | G | K | G | 0.80 |
| 7 | W | W | W | W | W | W | W | W | W | W | W | W | W | W | W | W | W | W | W | W | 1.00* |
| 8 | E | E | E | E | E | E | E | E | E | E | E | E | E | E | E | E | E | E | E | E | 1.00* |
| 9 | V | E | K | K | K | E | E | I | Q | M | K | Q | M | E | M | K | M | T | V | K M | 0.58 |
| 10 | R | R | R | R | R | R | R | R | R | K | R | R | R | R | A | R | R | A | R | A R | 0.79 |
| 11 | S | T | T | V | Q | I | V | Y | K | Y | Q | V | L | V | Y | T | L | Y | T | F Q | 0.38 |
| 12 | T | H | D | D | D | H | H | T | T | T | D | H | T | H | T | D | S | T | T | T T | 0.55 |
| 13 | V | T | S | S | - | L | T | A | A | S | P | V | N | S | E | T | E | E | V | D Q | 0.57 |
| 14 | S | D | N | T | N | D | D | A | S | E | T | D | T | D | D | N | D | R | S | S S | 0.62 |
| 15 | G | G | D | G | G | G | G | G | G | G | G | A | G | G | G | Y | G | G | G | G | 0.81 |
| 16 | R | R | R | R | R | R | E | R | V | R | R | R | R | E | R | H | E | R | E | R | 0.71 |
| 17 | I | V | V | V | V | T | V | R | V | R | M | V | V | T | V | V | V | L | I | V | V 0.64 |
| 18 | Y | F | Y | Y | Y | F | F | F | Y | Y | Y | F | Y | F | Y | Y | Y | Y | Y | Y | 0.90+ |
| 19 | F | F | F | F | Y | Y | Y | F | F | F | F | F | Y | F | F | F | F | F | F | F | 0.88+ |
| 20 | V | I | V | V | V | I | I | V | V | V | V | I | V | I | I | V | V | I | V | I V | 0.90+ |
| 21 | D | N | N | N | N | D | D | D | D | D | N | D | D | D | D | H | D | D | D | D | 0.85+ |
| 22 | H | H | H | H | H | H | H | H | H | H | H | H | H | H | H | H | H | H | H | H | 1.00* |
| 23 | N | N | N | N | N | N | N | N | N | N | V | N | N | N | N | P | S | N | N | N | 0.85+ |
| 24 | N | I | T | T | T | S | T | T | N | T | N | R | T | T | T | T | T | N | T | N | 0.66 |
| 25 | R | K | R | K | R | K | R | R | R | R | R | R | K | R | K | R | K | G | R | G R | 0.65 |
| 26 | T | K | I | T | T | I | T | R | T | T | T | R | T | N | T | T | T | T | T | T | 0.59 |
| 27 | T | T | T | T | T | T | T | T | T | T | T | T | T | T | T | T | T | S | T | S T | 1.00* |
| 28 | Q | Q | Q | Q | Q | Q | Q | T | Q | T | Q | Q | T | Q | S | Q | T | H | Q | H Q | 0.58 |
| 29 | F | W | W | W | W | W | W | F | F | W | W | W | W | W | W | W | W | F | W | F | 0.75 |
| 30 | T | E | E | E | E | E | E | E | T | K | E | E | D | E | V | E | S | L | T | L | 0.62 |
| 31 | D | D | D | D | D | D | D | D | D | D | D | D | D | D | D | D | D | D | D | D | 1.00* |
| 32 | P | P | P | P | P | P | P | P | P | P | P | P | P | P | P | P | P | P | P | P | 1.00* |
| 33 | R | R | R | R | R | R | R | R | R | R | R | R | R | R | R | R | R | R | R | R | 1.00* |
| 34 | L | L | - | - | - | L | L | - | I | - | - | F | L | L | - | - | - | L | L | L L | 0.94+ |
| 35 | - | Q | - | - | - | Q | - | - | N | - | - | - | - | Q | - | - | - | H | - | - - | 0.61 |

C-terminal end (down)

SEQ. ID.

2
7
8
9
10
11
12
13

TABLE 2-continued

Conservation of amino acids within WW-2 domains.

14
15
16
17
18
19
20
21
22
23
24
25
26

Example 4

Modeling of Smurf1-WW2 Domain, WW Domain Interacting Motifs of LMP-1

Proteins from different sources and some times diverse biological functions can have similar sequences, and it is generally accepted that high sequence similarity is reflected by distinct structural similarity. Indeed, the relative root mean square deviation (RMSD) of the alpha-carbon co-ordinates for protein cores sharing 50% residue identity is expected to be only around 1 Å. We have used the homologous regions of 1TK7:A and 1I5H:W structures as templates to model the Smurf1-WW2 domain structure using MODELLER as well as SWISS_MODEL software. The resultant structures are examined with PROCHECK software and the model structure (FIG. 2A) was optimized for stereo-chemical parameters. The resulting model (FIG. 2B) shows that the three anti-parallel β-sheets typical of WW domains along with conserved side-chain residues. Similarly we have also modeled the peptide motif structures of WW domain interacting site B of LMP-1 based on domain-Renac Bp2 peptide complex structure (PDB code: 1I5H), that interact with Smurf1 WW domain (FIG. 2C). The 1I5H complex has a peptide fragment with three proline residues in complex with WW domain. This peptide is similar to the 8-residue stretch of WW domain interacting site B in LMP-1 sequence.

Example 5

Modeling of Smurf1-WW2 Domain Interaction PPXY Motif of LMP-1

We have used AFFINITY for flexible docking of the peptide molecules on to the interaction surface of the Smurf1 WW2 domain model (FIG. 2D). We have used very closely related homologues of WW domain complex structures available in the database. We are quite certain that the model we generated for Smurf1 WW domain is accurately comparable to native structure including side chain atomic placements. A more similar complex structure is available in the database (PDB code: 1I5H) facilitating the placement of the modeled LMP-1 peptides at an appropriate location near to the interaction site to do accurate docking. The grid docking (AFFINITY) procedure was employed for the interaction for the WW domain interacting site of LMP-1 with WW2 domain of Smurf1 (FIG. 2D).

Our results on WW domain interaction with its target motif in LMP-1 are consistent with biochemical data reported for WW domain interacting motifs. Surface accessible area of residues of bound and unbound Smurf1 WW2 domain with its target motif has given information about specific residues that are involved in their complementary contact points. It can be seen from Table III that residues 10 (Arg), 18 (Tyr), 25 (Arg) and 27 (Thr) show more surface accessible area involved in interaction with LMP-1 peptide. However, Gln at position 28 also show considerable interaction area. These differences may result in differential binding affinity, functional differences and cellular regulation by these binding partners.

Example 6

In vitro Binding Studies with Purified Recombinant Smurf1 and LMP Proteins

We have expressed cDNAs for different isoforms of LMP with $(His)_6$-fusion tag using bacterial expression vector in *E. coli*. Similarly, we also expressed the $His_6$-fusion proteins for Smurf1 in *E. coli*.

*E. coli* XL1 blue and BL 21-codon plus (DE3)-RP (Stratagene) hosts were maintained on LB agar plates and grown at 37° C. in the presence of ampicillin at 100 mg/L. All cloning methods including PCR, restriction digestion, ligations, *E. coli* transformation and plasmid DNA were performed according to standard protocols. LMP-1, LMP-1t, LMP-2 and LMP-3 cDNAs were cloned into TAT-HA vector in XL1 blue host. LMP-1 mutants were generated using the following primers: hLMP1Mutant A forward primer: 5'-CGC-CCCCGCCGCGGACGCAGCACGGTACACCTTTGCAC-3' (SEQ. ID. NO. 47), hLMP1 Mutant A reverse primer: 5'-GTGCAAAGGTGTACCGTGCTGCGTCCGCGGCG GGGGCG-3' (SEQ ID. NO. 48), hLMP1 Mutant B forward primer: 5'-GGCCCGGCCCTTTGGGGCGGCA GCAG-CAGCTGACAGCGCCCCGCAAC-3' (SEQ. ID. NO. 49), hLMP1 Mutant B reverse primer: 5'-GTTGC GGGGCGCT-GTCAGCTGCTGCTGCCGCCCCAAAGGGCCGGGCC-3' (SEQ. ID. NO. 50). Smurf1 cDNA was cloned into pTrcHis vector (Invitrogen) and XL1 blue host. For generation of Smurf1ΔWW2 mutant the following primers were used: hSMURF1WW2 forward primer: 5'-GTGTGAACTGTGAT-GAACTTAATCACCAGTGCCAACTC-3' (SEQ. ID. NO. 51), hSmurf1 WW2 reverse primer: 5'-GAGTTGGCACTG-GTGATTAAGTTCATCACAGTTCACAC-3' (SEQ. ID. NO. 52). Mutagenesis was performed with Quikchange site-directed mutagenesis kit (Stratagene).

Bacterial cultures were grown at 37° C. until $O.D_{600}$ reached 0.8. IPTG was added to 200 uM and culture was continued to grow further 8 hrs at 37° C. Cells were harvested and pellets were suspended ice-cold lysis buffer (20 mM phosphate buffer, pH 7.0 containing 50 mM Tris-HCl, pH 7.5 and 0.5 M NaCl). The uniform cell suspension was sonicated (Sonicator, Model W-385, Heat systems-Ultrasonics, Inc.) 4×15 sec bursts at minimum power-out put settings in ice with 2 min interval between each burst. The lysate was centrifuged at 10,000 g (Beckman #17 Rotor, 13,000 RPM) at 4° C. and the supernatant and applied onto Sephacryl S-100/S-200 columns (HiPrep 16×60) using AKTA FPLC system with Unicorn 4.0 software (Amersham Pharmacia Biotech) at a flow rate of 1 ml/min. Fractions (2-4 ml) were collected immediately after the void volume (35 ml). Aliquots, from each fraction were assayed by slot blotting, SDS-PAGE and western blotting. The fractions, identified by western blots were pooled, dialyzed against 20 mM phosphate buffer, pH 7.5 containing NaCl (50 mM) and imidazole (20 mM) and applied to Ni++ affinity resin (Probond, Invitrogen) previously equilibrated with 4×10 ml of buffer. Non-specific proteins are washed off the column with 3×10 ml of 20 mM phosphate buffer, pH 6.0 containing NaCl (50 mM) and imidazole (20 mM). Affinity-bound proteins were eluted using 3×10 ml washes with 20 mM phosphate buffer, pH 4.0 containing NaCl (50 mM). Fractions containing desired protein were pooled (based on Western blot) and then concentrated and de-salted using the centriprep devices (Amicon). Protein quantitation was performed with protein assay reagent (Bio-Rad) using BSA as standard. The yield of recombinant protein was routinely about 0.75 to 1.0 mg of pure protein from every 2-liter culture.

The purity was determined by SDS-PAGE followed by gel staining and western blots using specific-antibodies to either Smurf1 or LMPs. LMPs are labeled with biotin as described in methods and the specific activity of biotin incorporation is normalized with avidin-HABA assay.

Example 7

Mutation of WW-Domain Interacting Site B Abolishes LMP-1 Binding to Smurf1

Site-directed mutants were prepared by introducing two Ala residues as substitution for two Pro residues in site A; three Ala residues as substitution for three Pro residues at site B in osteogenic region of LMP-1.

Purified protein ligands were prepared at 10 mg/ml concentration in 50 mM sodium borate buffer, pH 8.5; 0.5 M NaCl. Various amounts of sulfo-NHS-biotin (100 mM stock in DMSO) were mixed with protein ligand to achieve a molar ratio of sulfo-NHS-biotin/protein ligand of 10.0 in a 100 ul reaction volume. The reaction was carried in ice for 2 hr with occasional shaking and was then terminated with the addition of lysine at a final concentration of 20 mM. The un-reacted free biotin was removed by gel filtration and the concentrated labeled ligand was stored at −20° C. until use. The specific activity of biotin incorporation was normalized using avidin-HABA assay. Smurf1 protein was labeled using biotinylated lysine in a coupled in vitro transcription and translation system following the method recommended by the manufacturer (Promega).

Figure 3:
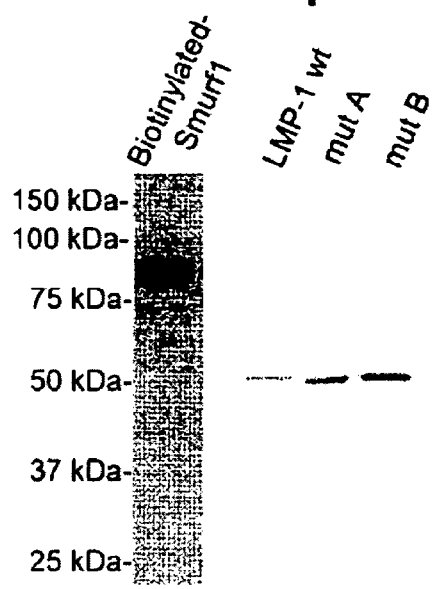
FIG. 3 is a photography of an SDS-PAGE gel demonstrating the purity and integrity of recombinant proteins (Smurf1, LMP wild type, LMP-1 mutant form A, and LMP-1 mutant form B) (FIG. 3A) and the results of the binding assays in ligand blots using biotin-labeled Smurf1 (FIG. 3B).
Figure 3:
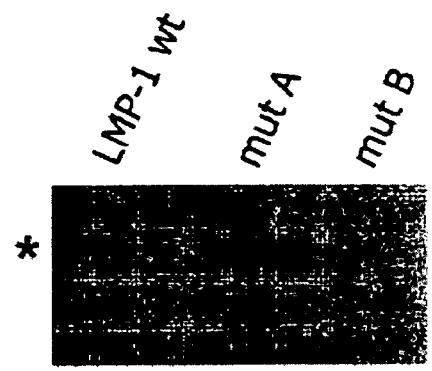

The purity and the integrity of isolated recombinant proteins (Smurf1, LMP wild type, mutant form A and B) are shown in FIG. 3, Panel A. The SDS-PAGE separated recombinant proteins showed predominantly single band at expected molecular sizes when detected by coomassie staining of gels. In the initial attempts on binding studies, Smurf1 proteins were separated by SDS-PAGE and trans-blotted the resolved proteins onto a nitrocellulose membrane. The WW-interacting motifs in LMPs are resistant to thermal denaturation or the nature of binding of this motif is somewhat independent of changes in conformation of the rest of the polypeptide. Binding assays in ligand blots using biotin-labeled Smurf1 were performed (FIG. 3, Panel B). Equal amounts of LMP-1 wild type and mutant A and mutant B were run in SDS-PAGE and blotted on to nitrocellulose membrane. The membranes were blocked with 5% milk protein to avoid non-specific binding. Blots are probed with biotin-labeled Smurf1 followed by incubating with neutravidin-linked horse radish peroxidase (HRP). The signals were detected by incubating chemiluminescent substrates and exposure to x-ray film. As shown in FIG. 3, Panel B, the wild type LMP-1 and the mutant A of LMP-1 bound to wild type Smurf1. The site A mutant showed similar binding to that of wild type LMP-1 where as the site B mutant showed loss of binding indicating that this site is necessary and is the primary determinant in Smurf1 binding.

Example 8

Ubiquitination of Smad1 by Smurf1 in vitro

Ubiquitination of purified Smad1 in an in vitro assay using reconstituted E1, E2 enzymes and the recombinant wild type and WW2Vmutant Smurf1 (E3 ligase) were performed.

Purified Smad1 (100 ng) was buffer-exchanged into ubiquitination buffer (50 uM Tris-HCl pH 8.0, 5 mM $MgCl_2$, 0.5 mM dithiothreitol (DTT), 2 mM NaF, and 3 uM okadaic acid). Smad1 is then combined with a mixture of purified E1 and E2 ligases and incubated with Smurf1 (E3 ligase) in the presence or absence of recombinant LMP-1 (1.0 uM or 10 uM) or LMP-2 (10 uM) proteins. The reaction mixture also contained 2 mM ATP, labeled ubiquitin (150 uM), ubiquitin aldehyde (5 uM), and creatine kinase-ATP generating system. The ubiquitin aldehyde was included to prevent hydrolysis of polyubiquitin chains. The reaction mixture (100 uL) was incubated up to 3 hr at 37° C. Aliquots at various time points are taken for SDS-PAGE and western blotting using specific antibody for Smad and/or ubiquitin. The ubiquitination reaction was also performed in the presence of LMP variants to determine the extent of inhibition by each of them.

Figure 4:
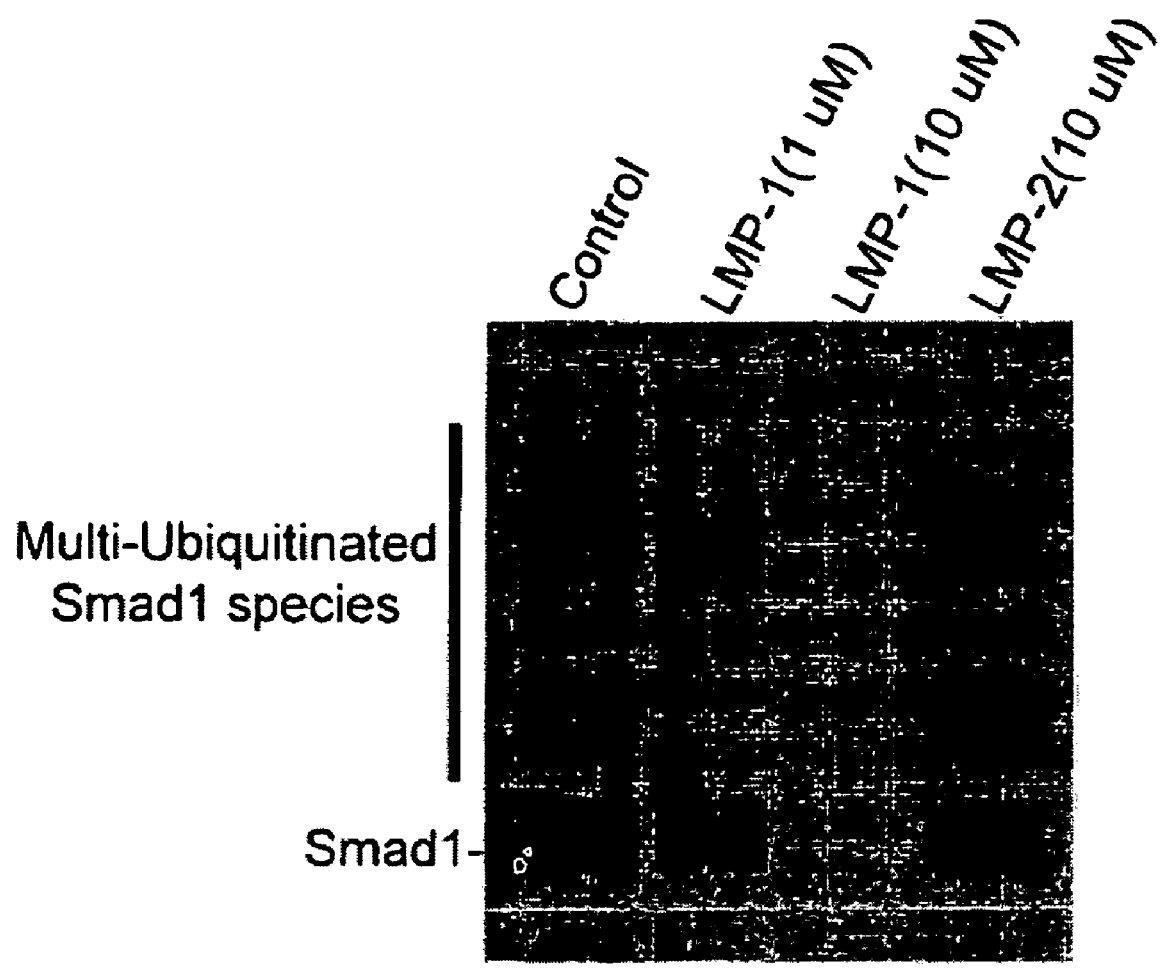
FIG. 4 is a photography of an SDS-PAGE gel demonstrating that LMP-1 inhibits ubiquitination of Smad1 by Smurf1 by competing with Smad1 for Smurf1 binding when used at 10 uM concentration.

The ubiquitination reaction products were separated by SDS-PAGE and analyzed by western blot using ubiquitin-specific rabbit primary antibody and HRP-linked second antibody (FIG. 4). The reaction mixture obtained with wild type Smurf1 in the absence of LMP-1 (lane 1) or in the presence of LMP-2 (lane 4) showed series of multi-ubiquitinated Smad1 whereas the reaction mixtures that contained LMP-1 (1 uM in lane 2; 10 uM in lane 3) showed concentration-dependent inhibition of the Smad1 ubiquitination by Smurf1 (FIG. 4; lane 4). The identity of Smad1 was confirmed by western blots with Smad1-specific antibodies. These results confirmed the observation in slot blot binding assay that the Smurf1 mutant failed binding to Smad1 and resulted in lack of ubiquitination by Smurf1. LMP-1 inhibited ubiquitination of Smad1 by Smurf1 by competing with Smad1 for Smurf1 binding when used at 10 uM concentration. LMP-2 which lacks WW domain interaction motifs, did not bind Smurf1 and thus did not inhibit ubiquitination of Smad1. Taken together, these results demonstrate that binding to WW2 domain is a pre-requirement for the successful ubiquitination of target proteins by Smurf1.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of identifying an agent affecting a binding between an LMP protein and a Smurf1 protein comprising:
   providing a first composition comprising:
      a first amino acid sequence comprising the amino acid sequence of SEQ ID NO: 41;
      a second amino acid sequence comprising an amino acid sequence at least 90% identical to SEQ ID NO: 2 and capable of binding the amino acid sequence of SEQ ID NO: 41; and
      the agent; and
   measuring an amount of a complex formed between the first amino acid sequence and the second amino acid sequence in the first composition; and
      comparing the amount of the complex in the first composition with an amount of a complex formed between a third amino acid sequence and a fourth amino acid sequence in a second composition, wherein:
      said second composition does not include the agent;
      the third amino acid sequence comprises the amino acid sequence of SEQ ID NO: 41: and
      the fourth amino acid sequence comprises an amino acid sequence at least 90% identical to SEQ ID NO: 2 and capable of binding the amino acid sequence of SEQ ID NO: 41, and wherein further each of said second and said fourth amino acid sequences comprises:
   leucine at a position corresponding to position 3 of SEQ ID NO: 2;
   proline at a position corresponding to position 4 of SEQ ID NO: 2;
   tryptophan at a position corresponding to position 7 of SEQ ID NO: 2;
   glutamic acid at a position corresponding to position 8 of SEQ ID NO: 2;
   arginine, lysine or alanine at a position corresponding to position 10 of SEQ ID NO: 2;
   tyrosine, phenylalanine or isoleucine at a position corresponding to position 18 of SEQ ID NO: 2;
   phenylalanine or isoleucine at a position corresponding to position 19 of SEQ ID NO: 2;
   valine or isoleucine at a position corresponding to position 20 of SEQ ID NO: 2;
   asparagine or aspartic acid at a position corresponding to position 21 of SEQ ID NO: 2;
   histidine at a position corresponding to position 22 of SEQ ID NO: 2;
   asparagine, valine, proline or serine at a position corresponding to position 23 of SEQ ID NO:2;
   arginine or lysine at a position corresponding to position 25 of SEQ ID NO: 2;
   serine or threonine at a position corresponding to position 27 of SEQ ID NO: 2;
   glutamine at a position corresponding to position 28 of SEQ ID NO: 2;
   aspartic acid at a position corresponding to position 31 of SEQ ID NO: 2;
   proline at a position corresponding to position 32 of SEQ ID NO: 2; and
   arginine at a position corresponding to position 33 of SEQ ID NO: 2.

2. The method of claim 1, wherein each of said second and fourth sequence comprises SEQ ID NO: 2 and is capable of binding the amino acid sequence of SEQ ID NO: 41.

3. The method of claim 1, wherein
   an increased amount of the complex in the first composition indicates that the agent induces binding between the first amino acid sequence and the second amino acid sequence; and
   a decreased amount of the complex in the first composition indicates that the agent inhibits binding between the first amino acid sequence and the second amino acid sequence.

4. The method of claim 1, wherein
   an increased amount of the complex in the first composition indicates that the agent inhibits ubiquitination of a Smad protein by Smurf1; and
   a decreased amount of the complex in the first composition indicates that the agent induces ubiquitination of a Smad protein by Smurf1.

5. The method of claim 4, wherein the Smad protein is selected from the group consisting of a Smad1 protein, a Smad5 protein, and a Smad6 protein.

6. The method of claim 1, wherein
   an increased amount of the complex in the first composition indicates that the agent induces an osteogenic effect of an LMP protein or a fragment thereof; and
   a decreased amount of the complex in the first composition indicates that the agent inhibits an osteogenic effect of an LMP protein or a fragment thereof.

7. The method of claim 6, wherein the LMP protein or the fragment thereof is selected from the group consisting of LMP-1, corresponding to SEQ ID NO: 53, LMP-3 corresponding to SEQ ID NO: 54, and LMP-1s corresponding to SEQ ID NO: 55.

8. The method of claim 2, wherein
   the first amino acid sequence is identical to the third amino acid sequence, or
   the second amino acid sequence is identical to the fourth amino acid sequence, or
   the first amino acid sequence is identical to the third amino acid sequence and the second amino acid sequence is identical to the fourth amino acid sequence.

9. The method of claim 1, wherein the SEQ ID NO: 41 is incorporated within SEQ ID NO: 4.

10. The method of claim 1, wherein the amino acid sequence at least 90% identical to SEQ ID NO. 2 and capable of binding the amino acid sequence of SEQ ID NO: 41 is 100% identical to SEQ ID NO. 2.

11. The method of claim 1, wherein the amino acid sequence at least 90% identical to SEQ ID NO: 2 comprises:
   arginine at a position corresponding to position 10 of SEQ ID NO: 2;
   tyrosine at a position corresponding to position 18 of SEQ ID NO: 2;
   arginine at a position corresponding to position 25 of SEQ ID NO: 2;
   threonine at a position corresponding to position 27 of SEQ ID NO 2.

12. The method of claim 1, wherein the first composition and the second composition are cell-free systems.

* * * * *

SEQUENCE LISTING

```
<160> NUMBER OF SEQ ID NOS: 56

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid

<400> SEQUENCE: 1

Pro Pro Xaa Xaa
  1

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Pro Leu Pro Pro Gly Trp Glu Val Arg Ser Thr Val Ser Gly Arg
  1               5                  10                  15

Ile Tyr Phe Val Asp His Asn Asn Arg Thr Thr Gln Phe Thr Asp Pro
             20                  25                  30

Arg Leu

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Asp Pro Pro Arg Tyr Thr Phe Ala Pro
  1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Pro Pro Pro Ala Asp Ser Ala Pro
  1               5                  10

<210> SEQ ID NO 5
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 5

Pro Pro Pro Ala
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Pro Ala Arg
  1

<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Pro Leu Pro Pro Gly Trp Glu Glu Arg Thr His Thr Asp Gly Arg
  1               5                  10                  15

Val Phe Phe Ile Asn His Asn Ile Lys Lys Thr Gln Trp Glu Asp Pro
                 20                  25                  30

Arg Leu Gln
         35

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Pro Leu Pro Pro Gly Trp Glu Lys Arg Thr Asp Ser Asn Gly Arg
  1               5                  10                  15

Val Tyr Phe Val Asn His Asn Thr Arg Ile Thr Gln Trp Glu Asp Pro
                 20                  25                  30

Arg

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Pro Leu Pro Pro Gly Trp Glu Lys Arg Val Asp Ser Thr Asp Arg
  1               5                  10                  15

Val Tyr Phe Val Asn His Asn Thr Lys Thr Thr Gln Trp Glu Asp Pro
                 20                  25                  30

Arg
```

-continued

```
<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Pro Leu Pro Pro Gly Trp Glu Lys Arg Gln Asp Asn Gly Arg Val
 1               5                  10                  15

Tyr Tyr Val Asn His Asn Thr Arg Thr Thr Gln Trp Glu Asp Pro Arg
            20                  25                  30

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Pro Leu Pro Pro Gly Trp Glu Glu Arg Ile His Leu Asp Gly Arg
 1               5                  10                  15

Thr Phe Tyr Ile Asp His Asn Ser Lys Ile Thr Gln Trp Glu Asp Pro
            20                  25                  30

Arg Leu Gln
        35

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Pro Leu Pro Glu Gly Trp Glu Glu Arg Val His Thr Asp Gly Arg
 1               5                  10                  15

Val Phe Tyr Ile Asp His Asn Thr Arg Thr Thr Gln Trp Glu Asp Pro
            20                  25                  30

Arg Leu

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Leu Pro Pro Gly Trp Glu Ile Arg Tyr Thr Ala Ala Gly Glu
 1               5                  10                  15

Arg Phe Phe Val Asp His Asn Thr Arg Arg Thr Thr Phe Glu Asp Pro
            20                  25                  30

Arg

<210> SEQ ID NO 14
<211> LENGTH: 35
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Leu Pro His Gly Trp Glu Gln Arg Lys Thr Ala Ser Gly Arg
 1               5                  10                  15

Val Tyr Phe Val Asp His Asn Asn Arg Thr Thr Gln Phe Thr Asp Pro
                20                  25                  30

Arg Ile Asn
        35

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Pro Pro Gly Trp Glu Met Lys Tyr Thr Ser Glu Gly Val Arg Tyr
 1               5                  10                  15

Phe Val Asp His Asn Thr Arg Thr Thr Thr Phe Lys Asp Pro Arg
                20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Pro Leu Pro Glu Gly Trp Glu Lys Arg Gln Asp Pro Thr Gly Arg
 1               5                  10                  15

Met Tyr Phe Val Asn His Val Asn Arg Thr Thr Gln Trp Glu Asp Pro
                20                  25                  30

Arg

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ala Leu Pro Pro Gly Trp Glu Gln Arg Val His Val Asp Gly Arg
 1               5                  10                  15

Val Phe Phe Ile Asp His Asn Arg Arg Arg Thr Gln Trp Glu Asp Pro
                20                  25                  30

Arg Phe

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 18

Gly Pro Leu Pro Ser Gly Trp Glu Met Arg Leu Thr Asn Thr Ala Arg
1               5                   10                  15

Val Tyr Phe Val Asp His Asn Thr Lys Thr Thr Thr Trp Asp Asp Pro
            20                  25                  30

Arg Leu

<210> SEQ ID NO 19
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Pro Leu Pro Pro Gly Trp Glu Glu Arg Val His Ser Asp Gly Arg
1               5                   10                  15

Thr Phe Tyr Ile Asp His Asn Thr Arg Asn Thr Gln Trp Glu Asp Pro
            20                  25                  30

Arg Leu Gln
        35

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Leu Pro Glu Asn Trp Glu Met Ala Tyr Thr Glu Asp Gly Glu
1               5                   10                  15

Val Tyr Phe Ile Asp His Asn Thr Lys Thr Thr Ser Trp Val Asp Pro
            20                  25                  30

Arg

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Pro Leu Pro His Gly Trp Glu Lys Arg Thr Asp Thr Asn Gly Arg
1               5                   10                  15

Val Tyr Phe Val His His Pro Thr Arg Thr Thr Gln Trp Glu Asp Pro
            20                  25                  30

Arg

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 22

Gly Pro Leu Pro Ala Gly Trp Glu Met Arg Leu Ser Glu Asp Tyr His
 1               5                  10                  15

Val Tyr Phe Val Asp His Ser Thr Lys Thr Thr Thr Trp Ser Asp Pro
            20                  25                  30

Arg

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Pro Leu Pro Pro Lys Trp Glu Thr Ala Tyr Thr Glu Arg Gly Glu
 1               5                  10                  15

Leu Tyr Phe Ile Asp His Asn Thr Gly Thr Ser His Trp Leu Asp Pro
            20                  25                  30

Arg Leu His
        35

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Leu Pro Ala Gly Trp Glu Val Arg Thr Thr Val Ser Gly Arg
 1               5                  10                  15

Ile Tyr Phe Val Asp His Asn Asn Arg Thr Thr Gln Phe Thr Asp Pro
            20                  25                  30

Arg Leu

<210> SEQ ID NO 25
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Pro Leu Pro Pro Lys Trp Glu Lys Ala Phe Thr Asp Ser Gly Glu
 1               5                  10                  15

Val Tyr Phe Ile Asp His Asn Thr Gly Thr Ser His Trp Leu Asp Pro
            20                  25                  30

Arg Leu

<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

-continued

```
Gly Pro Leu Pro Ser Gly Trp Glu Met Arg Gln Thr Gln Ser Gly Arg
1               5                   10                  15

Val Tyr Phe Val Asp His Asn Asn Arg Thr Thr Gln Phe Thr Asp Pro
            20                  25                  30

Arg Leu

<210> SEQ ID NO 27
<211> LENGTH: 731
<212> TYPE: PRT
<213> ORGANISM: Homo sapiens

<400> SEQUENCE: 27

Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
            20                  25                  30

Leu Pro Asp Pro Phe Ala Lys Ile Val Val Asp Gly Ser Gly Gln Cys
        35                  40                  45

His Ser Thr Asp Thr Val Lys Asn Thr Leu Asp Pro Lys Trp Asn Gln
    50                  55                  60

His Tyr Asp Leu Tyr Val Gly Lys Thr Asp Ser Ile Thr Ile Ser Val
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
            100                 105                 110

Tyr Gln Arg Leu Asp Leu Cys Lys Leu Asn Pro Ser Asp Thr Asp Ala
        115                 120                 125

Val Arg Gly Gln Ile Val Val Ser Leu Gln Thr Arg Asp Arg Ile Gly
    130                 135                 140

Thr Gly Gly Ser Val Val Asp Cys Arg Gly Leu Leu Glu Asn Glu Gly
145                 150                 155                 160

Thr Val Tyr Glu Asp Ser Gly Pro Gly Arg Pro Leu Ser Cys Phe Met
                165                 170                 175

Glu Glu Pro Ala Pro Tyr Thr Asp Ser Thr Gly Ala Ala Ala Gly Gly
            180                 185                 190

Gly Asn Cys Arg Phe Val Glu Ser Pro Ser Gln Asp Gln Arg Leu Gln
        195                 200                 205

Ala Gln Arg Leu Arg Asn Pro Asp Val Arg Gly Ser Leu Gln Thr Pro
    210                 215                 220

Gln Asn Arg Pro His Gly His Gln Ser Pro Glu Leu Pro Glu Gly Tyr
225                 230                 235                 240

Glu Gln Arg Thr Thr Val Gln Gly Gln Val Tyr Phe Leu His Thr Gln
                245                 250                 255

Thr Gly Val Ser Thr Trp His Asp Pro Arg Ile Pro Arg Asp Leu Asn
            260                 265                 270

Ser Val Asn Cys Asp Glu Leu Gly Pro Leu Pro Pro Gly Trp Glu Val
        275                 280                 285

Arg Ser Thr Val Ser Gly Arg Ile Tyr Phe Val Asp His Asn Asn Arg
    290                 295                 300

Thr Thr Gln Phe Thr Asp Pro Arg Leu His His Ile Met Asn His Gln
305                 310                 315                 320

Cys Gln Leu Lys Glu Pro Ser Gln Pro Leu Pro Leu Pro Ser Glu Gly
                325                 330                 335
```

Ser Leu Glu Asp Glu Leu Pro Ala Gln Arg Tyr Glu Arg Asp Leu
            340                 345                 350

Val Gln Lys Leu Lys Val Leu Arg His Glu Leu Ser Leu Gln Gln Pro
        355                 360                 365

Gln Ala Gly His Cys Arg Ile Glu Val Ser Arg Glu Glu Ile Phe Glu
    370                 375                 380

Glu Ser Tyr Arg Gln Ile Met Lys Met Arg Pro Lys Asp Leu Lys Lys
385                 390                 395                 400

Arg Leu Met Val Lys Phe Arg Gly Glu Gly Leu Asp Tyr Gly Gly
                405                 410                 415

Val Ala Arg Glu Trp Leu Tyr Leu Leu Cys His Glu Met Leu Asn Pro
            420                 425                 430

Tyr Tyr Gly Leu Phe Gln Tyr Ser Thr Asp Asn Ile Tyr Met Leu Gln
        435                 440                 445

Ile Asn Pro Asp Ser Ser Ile Asn Pro Asp His Leu Ser Tyr Phe His
    450                 455                 460

Phe Val Gly Arg Ile Met Gly Leu Ala Val Phe His Gly His Tyr Ile
465                 470                 475                 480

Asn Gly Gly Phe Thr Val Pro Phe Tyr Lys Gln Leu Leu Gly Lys Pro
                485                 490                 495

Ile Gln Leu Ser Asp Leu Glu Ser Val Asp Pro Glu Leu His Lys Ser
        500                 505                 510

Leu Val Trp Ile Leu Glu Asn Asp Ile Thr Pro Val Leu Asp His Thr
    515                 520                 525

Phe Cys Val Glu His Asn Ala Phe Gly Arg Ile Leu Gln His Glu Leu
530                 535                 540

Lys Pro Asn Gly Arg Asn Val Pro Val Thr Glu Glu Asn Lys Lys Glu
545                 550                 555                 560

Tyr Val Arg Leu Tyr Val Asn Trp Arg Phe Met Arg Gly Ile Glu Ala
                565                 570                 575

Gln Phe Leu Ala Leu Gln Lys Gly Phe Asn Glu Leu Ile Pro Gln His
        580                 585                 590

Leu Leu Lys Pro Phe Asp Gln Lys Glu Leu Glu Leu Ile Ile Gly Gly
    595                 600                 605

Leu Asp Lys Ile Asp Leu Asn Asp Trp Lys Ser Asn Thr Arg Leu Lys
610                 615                 620

His Cys Val Ala Asp Ser Asn Ile Val Arg Trp Phe Trp Gln Ala Val
625                 630                 635                 640

Glu Thr Phe Asp Glu Glu Arg Arg Ala Arg Leu Leu Gln Phe Val Thr
                645                 650                 655

Gly Ser Thr Arg Val Pro Leu Gln Gly Phe Lys Ala Leu Gln Gly Ser
        660                 665                 670

Thr Gly Ala Ala Gly Pro Arg Leu Phe Thr Ile His Leu Ile Asp Ala
    675                 680                 685

Asn Thr Asp Asn Leu Pro Lys Ala His Thr Cys Phe Asn Arg Ile Asp
690                 695                 700

Ile Pro Pro Tyr Glu Ser Tyr Glu Lys Leu Tyr Glu Lys Leu Leu Thr
705                 710                 715                 720

Ala Val Glu Glu Thr Cys Gly Phe Ala Val Glu
                725                 730

<210> SEQ ID NO 28
<211> LENGTH: 731
<212> TYPE: PRT

<213> ORGANISM: Xenopus laevis

<400> SEQUENCE: 28

```
Met Ser Asn Val Val Thr Arg Arg Gly Gly Ser Ser Ile Arg Val Arg
  1               5                  10                  15
Leu Thr Val Leu Cys Ala Lys Asn Leu Ala Lys Arg Asp Phe Phe Arg
                 20                  25                  30
Leu Pro Asp Pro Phe Ala Lys Ile Val Val Asp Gly Ser Gly Gln Cys
             35                  40                  45
His Ser Thr Asp Thr Val Lys Asn Thr Leu Asp Pro Lys Trp Asn Gln
         50                  55                  60
His Tyr Asp Leu Tyr Val Gly Lys Met Asp Ser Ile Thr Ile Ser Ile
 65                  70                  75                  80
Trp Asn His Lys Lys Ile His Lys Lys Gln Gly Ala Gly Phe Leu Gly
                 85                  90                  95
Cys Val Arg Leu Leu Ser Asn Ala Ile Ser Arg Leu Lys Asp Thr Gly
                100                 105                 110
Tyr Gln Arg Leu Asp Leu Cys Lys Leu Asn Pro Thr Asp Asn Asp Ala
            115                 120                 125
Val Arg Gly Gln Ile Val Val Ser Leu Gln Thr Arg Asp Arg Ile Gly
        130                 135                 140
Thr Leu Gly Ser Val Val Asp Cys Arg Gly Leu Leu Asp Asn Glu Gly
145                 150                 155                 160
Ala Leu Leu Glu Asp Thr Gly Pro Gly Arg Pro Leu Ser Cys Phe Met
                165                 170                 175
Asp Glu Pro Ala Pro Tyr Thr Asp Gly Pro Gly Ala Ala Gly Gly Gly
            180                 185                 190
Pro Gly Arg Leu Val Glu Ser Pro Gly Gln Glu Gln Arg Leu Gln Ala
        195                 200                 205
Gln Arg Val Arg Gly Pro Glu Val Arg Glu His Val Gln Thr Pro Gln
    210                 215                 220
Asn Arg Ser His Gly Phe Gln Ser Gln Asp Leu Pro Glu Gly Tyr Glu
225                 230                 235                 240
Gln Arg Thr Thr Val Gln Gly Gln Val Tyr Phe Leu His Thr Gln Thr
                245                 250                 255
Gly Val Ser Thr Trp His Asp Pro Arg Ile Pro Arg Asp Leu Asn Ser
            260                 265                 270
Val Asn Cys Asp Asp Leu Gly Ser Leu Pro Ala Gly Trp Glu Val Arg
        275                 280                 285
Thr Thr Val Ser Gly Arg Ile Tyr Phe Val Asp His Asn Asn Arg Thr
    290                 295                 300
Thr Gln Phe Thr Asp Pro Arg Leu His His Ile Ile Asn His Gln Ser
305                 310                 315                 320
Gln Leu Lys Glu Pro Asn His Ala Ile Pro Val Gln Ser Asp Gly Ser
                325                 330                 335
Leu Glu Asp Gly Asp Glu Phe Pro Ala Gln Arg Tyr Glu Arg Asp Leu
            340                 345                 350
Val Gln Lys Leu Lys Val Leu Arg His Glu Leu Ser Leu Leu Gln Pro
        355                 360                 365
Gln Ala Gly His Cys Arg Val Glu Val Ser Arg Glu Ile Phe Glu
    370                 375                 380
Glu Ser Tyr Arg Gln Ile Met Lys Met Arg Pro Lys Asp Leu Lys Lys
385                 390                 395                 400
```

-continued

```
Arg Leu Met Val Lys Phe Arg Gly Glu Glu Gly Leu Asp Tyr Gly Gly
                405                 410                 415

Val Ala Arg Glu Trp Leu Tyr Leu Leu Cys His Glu Met Leu Asn Pro
            420                 425                 430

Tyr Tyr Gly Leu Phe Gln Tyr Ser Thr Asp Asn Ile Tyr Thr Leu Gln
        435                 440                 445

Ile Asn Pro Asp Ser Ser Ile Asn Pro Asp His Leu Ser Tyr Phe His
    450                 455                 460

Phe Val Gly Arg Ile Met Gly Leu Ala Val Phe His Gly His Tyr Ile
465                 470                 475                 480

Asn Gly Gly Phe Thr Val Pro Phe Tyr Lys Gln Leu Leu Gly Lys Pro
                485                 490                 495

Ile Gln Leu Ser Asp Leu Glu Ser Val Asp Pro Glu Leu His Lys Ser
            500                 505                 510

Leu Val Trp Ile Leu Glu Asn Asp Ile Thr Ser Val Leu Asp His Thr
        515                 520                 525

Phe Cys Val Glu His Asn Ala Phe Gly Arg Leu Leu Gln His Glu Leu
    530                 535                 540

Lys Pro Asn Gly Lys Asn Leu Gln Val Thr Glu Asn Lys Lys Glu
545                 550                 555                 560

Tyr Val Arg Leu Tyr Val Asn Trp Arg Phe Met Arg Gly Ile Glu Ala
                565                 570                 575

Gln Phe Leu Ala Leu Gln Lys Gly Phe Asn Glu Leu Ile Pro Gln His
            580                 585                 590

Leu Leu Lys Pro Phe Glu Gln Lys Glu Leu Glu Leu Ile Ile Gly Gly
        595                 600                 605

Leu Asp Lys Ile Asp Ile Ser Asp Trp Lys Ala Asn Thr Arg Leu Lys
    610                 615                 620

His Cys Leu Ala Asn Ser Asn Ile Val Gln Trp Phe Trp Gln Ala Val
625                 630                 635                 640

Glu Ser Phe Asp Glu Glu Arg Arg Ala Arg Leu Leu Gln Phe Val Thr
                645                 650                 655

Gly Ser Thr Arg Val Pro Leu Gln Gly Phe Lys Ala Leu Gln Gly Ser
            660                 665                 670

Thr Gly Ala Ala Gly Pro Arg Leu Phe Thr Ile His Leu Ile Asp Ala
        675                 680                 685

Asn Thr Asp Asn Leu Pro Lys Ala His Thr Cys Phe Asn Arg Ile Asp
    690                 695                 700

Ile Pro Pro Tyr Glu Ser Tyr Glu Lys Leu Tyr Glu Lys Leu Leu Thr
705                 710                 715                 720

Ala Val Glu Glu Thr Ser Gly Phe Ala Val Glu
                725                 730

<210> SEQ ID NO 29
<211> LENGTH: 731
<212> TYPE: PRT
<213> ORGANISM: Mus musculus

<400> SEQUENCE: 29

Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
            20                  25                  30

Leu Pro Asp Pro Phe Ala Lys Ile Val Val Asp Gly Ser Gly Gln Cys
        35                  40                  45
```

-continued

```
His Ser Thr Asp Thr Val Lys Asn Thr Leu Asp Pro Lys Trp Asn Gln
         50                  55                  60
His Tyr Asp Leu Tyr Val Gly Lys Thr Asp Ser Ile Thr Ile Ser Val
 65                  70                  75                  80
Trp Asn His Lys Lys Ile His Lys Lys Gln Gly Ala Gly Phe Leu Gly
                 85                  90                  95
Cys Val Arg Leu Leu Ser Asn Ala Ile Ser Arg Leu Lys Asp Thr Gly
                100                 105                 110
Tyr Gln Arg Leu Asp Leu Cys Lys Leu Asn Pro Ser Asp Thr Asp Ala
                115                 120                 125
Val Arg Gly Gln Ile Val Val Ser Leu Gln Thr Arg Asp Arg Ile Gly
            130                 135                 140
Gly Gly Gly Ser Val Val Asp Cys Arg Gly Leu Glu Asn Glu Gly
145                 150                 155                 160
Thr Val Tyr Glu Asp Ser Gly Pro Gly Arg Pro Leu Ser Cys Leu Met
                165                 170                 175
Glu Glu Pro Ala Pro Tyr Thr Asp Gly Thr Gly Ala Ala Ala Gly Gly
            180                 185                 190
Gly Asn Cys Arg Phe Val Glu Ser Pro Ser Gln Asp Gln Arg Leu Leu
        195                 200                 205
Val Gln Arg Leu Arg Asn Pro Glu Val Arg Gly Pro Leu Gln Thr Pro
    210                 215                 220
Gln Asn Arg Pro His Gly His Gln Ser Pro Glu Leu Pro Glu Gly Tyr
225                 230                 235                 240
Glu Gln Arg Thr Thr Val Gln Gly Gln Val Tyr Phe Leu His Thr Gln
                245                 250                 255
Thr Gly Val Ser Thr Trp His Asp Pro Arg Ile Pro Arg Asp Leu Asn
                260                 265                 270
Ser Val Asn Cys Asp Glu Leu Gly Pro Leu Pro Pro Gly Trp Glu Val
                275                 280                 285
Arg Ser Thr Val Ser Gly Arg Ile Tyr Phe Val Asp His Asn Asn Arg
    290                 295                 300
Thr Thr Gln Phe Thr Asp Pro Arg Leu His His Ile Met Asn His Gln
305                 310                 315                 320
Cys Gln Leu Lys Glu Pro Ser Gln Pro Leu Gln Leu Pro Ser Glu Gly
                325                 330                 335
Ser Val Glu Asp Glu Glu Leu Pro Ala Gln Arg Tyr Glu Arg Asp Leu
                340                 345                 350
Val Gln Lys Leu Lys Val Leu Arg His Glu Leu Ser Leu Gln Gln Pro
            355                 360                 365
Gln Ala Gly His Cys Arg Ile Glu Val Ser Arg Glu Glu Ile Phe Glu
        370                 375                 380
Glu Ser Tyr Arg Gln Ile Met Lys Met Arg Pro Lys Asp Leu Lys Lys
385                 390                 395                 400
Arg Leu Met Val Lys Phe Arg Gly Glu Glu Gly Leu Asp Tyr Gly Gly
                405                 410                 415
Val Ala Arg Glu Trp Leu Tyr Leu Leu Cys His Glu Met Leu Asn Pro
                420                 425                 430
Tyr Tyr Gly Leu Phe Gln Tyr Ser Thr Asp Asn Ile Tyr Thr Leu Gln
            435                 440                 445
Ile Asn Pro Asp Ser Ser Ile Asn Pro Asp His Leu Ser Tyr Phe His
    450                 455                 460
```

```
Phe Val Gly Arg Ile Met Gly Leu Ala Val Phe His Gly His Tyr Ile
465                 470                 475                 480

Asn Gly Gly Phe Thr Val Pro Phe Tyr Lys Gln Leu Leu Gly Lys Pro
                485                 490                 495

Ile Gln Leu Ser Asp Leu Glu Ser Val Asp Pro Glu Leu His Lys Ser
            500                 505                 510

Leu Val Trp Ile Leu Glu Asn Asp Ile Thr Pro Val Leu Asp His Thr
        515                 520                 525

Phe Cys Val Glu His Asn Ala Phe Gly Arg Ile Leu Gln His Glu Leu
    530                 535                 540

Lys Pro Asn Gly Arg Asn Val Pro Val Thr Glu Asn Lys Lys Glu
545                 550                 555                 560

Tyr Val Arg Leu Tyr Val Asn Trp Arg Phe Met Arg Gly Ile Glu Ala
                565                 570                 575

Gln Phe Leu Ala Leu Gln Lys Gly Phe Asn Glu Leu Ile Pro Gln His
            580                 585                 590

Leu Leu Lys Pro Phe Asp Gln Lys Glu Leu Glu Leu Ile Ile Gly Gly
        595                 600                 605

Leu Asp Lys Ile Asp Leu Asn Asp Trp Lys Ser Asn Thr Arg Leu Lys
    610                 615                 620

His Cys Val Ala Asp Ser Asn Ile Val Arg Trp Phe Trp Gln Ala Val
625                 630                 635                 640

Glu Thr Phe Asp Glu Glu Arg Arg Ala Arg Leu Leu Gln Phe Val Thr
                645                 650                 655

Gly Ser Thr Arg Val Pro Leu Gln Gly Phe Lys Ala Leu Gln Gly Ser
            660                 665                 670

Thr Gly Ala Ala Gly Pro Arg Leu Phe Thr Ile His Leu Ile Asp Ala
        675                 680                 685

Asn Thr Asp Asn Leu Pro Lys Ala His Thr Cys Phe Asn Arg Ile Asp
    690                 695                 700

Ile Pro Pro Tyr Glu Ser Tyr Glu Lys Leu Tyr Glu Lys Leu Leu Thr
705                 710                 715                 720

Ala Val Glu Glu Thr Cys Gly Phe Ala Val Glu
                725                 730

<210> SEQ ID NO 30
<211> LENGTH: 794
<212> TYPE: PRT
<213> ORGANISM: Pan troglodytes

<400> SEQUENCE: 30

Met Gly Val Lys Thr Ala Gly Val Ser Leu Cys Ile Val Pro Gly Val
1               5                   10                  15

Trp Arg Val Pro Ala Leu Thr Ala Glu Glu Asn Tyr Thr Val Asp Ser
                20                  25                  30

His Tyr Ser Gln Asp Tyr Ser Glu Leu Arg Gln Ser Ser Leu Val Asn
            35                  40                  45

Ala Gln Thr Leu Arg Glu Thr Leu Leu Cys Ala Lys Asn Leu Ala Lys
        50                  55                  60

Lys Asp Phe Phe Arg Leu Pro Asp Pro Phe Ala Lys Ile Val Val Asp
65                  70                  75                  80

Gly Ser Gly Gln Cys His Ser Thr Asp Thr Val Lys Asn Thr Leu Asp
                85                  90                  95

Pro Lys Trp Asn Gln His Tyr Asp Leu Tyr Val Gly Lys Thr Asp Ser
            100                 105                 110
```

```
Ile Thr Ile Ser Val Trp Asn His Lys Lys Ile His Lys Lys Gln Gly
        115                 120                 125

Ala Gly Phe Leu Gly Cys Val Arg Leu Leu Ser Asn Ala Ile Ser Arg
    130                 135                 140

Leu Lys Asp Thr Gly Tyr Gln Arg Leu Asp Leu Cys Lys Leu Asn Pro
145                 150                 155                 160

Ser Asp Thr Asp Ala Val Arg Gly Gln Ile Val Val Ser Leu Gln Thr
                165                 170                 175

Arg Asp Arg Ile Gly Thr Gly Gly Ser Val Val Asp Cys Arg Gly Leu
            180                 185                 190

Leu Glu Asn Glu Gly Thr Val Tyr Glu Asp Ser Gly Pro Gly Arg Pro
        195                 200                 205

Leu Ser Cys Phe Met Glu Glu Pro Ala Pro Tyr Thr Asp Ser Thr Gly
    210                 215                 220

Ala Ala Ala Gly Gly Gly Asn Cys Arg Phe Val Glu Ser Pro Ser Gln
225                 230                 235                 240

Asp Gln Arg Leu Gln Ala Gln Arg Leu Arg Asn Pro Asp Val Arg Gly
                245                 250                 255

Ser Leu Gln Thr Pro Gln Asn Arg Pro His Gly His Gln Ser Pro Glu
            260                 265                 270

Leu Pro Glu Gly Tyr Glu Gln Arg Thr Thr Val Gln Gly Gln Val Tyr
        275                 280                 285

Phe Leu His Thr Gln Thr Gly Val Ser Thr Trp His Asp Pro Arg Ile
    290                 295                 300

Pro Ser Pro Ser Gly Thr Ile Pro Gly Gly Asp Ala Ala Phe Leu Tyr
305                 310                 315                 320

Glu Phe Leu Leu Gln Gly His Thr Ser Glu Pro Arg Asp Leu Asn Ser
                325                 330                 335

Val Asn Cys Asp Glu Leu Gly Pro Leu Pro Gly Trp Glu Val Arg
            340                 345                 350

Ser Thr Val Ser Gly Arg Ile Tyr Phe Val Asp His Asn Asn Arg Thr
        355                 360                 365

Thr Gln Phe Thr Asp Pro Arg Leu His His Ile Met Asn His Gln Cys
    370                 375                 380

Gln Leu Lys Glu Pro Ser Gln Pro Leu Pro Leu Pro Ser Glu Gly Ser
385                 390                 395                 400

Leu Glu Asp Glu Glu Leu Pro Ala Gln Arg Tyr Glu Arg Asp Leu Val
                405                 410                 415

Gln Lys Leu Lys Val Leu Arg His Glu Leu Ser Leu Gln Gln Pro Gln
            420                 425                 430

Ala Gly His Cys Arg Ile Glu Val Ser Arg Glu Glu Ile Phe Glu Glu
        435                 440                 445

Ser Tyr Arg Gln Ile Met Lys Met Arg Pro Lys Asp Leu Lys Lys Arg
    450                 455                 460

Leu Met Val Lys Phe Arg Gly Glu Glu Gly Leu Asp Tyr Gly Gly Val
465                 470                 475                 480

Ala Arg Glu Trp Leu Tyr Leu Leu Cys His Glu Met Leu Asn Pro Tyr
                485                 490                 495

Tyr Gly Leu Phe Gln Tyr Ser Thr Asp Asn Ile Tyr Met Leu Gln Ile
            500                 505                 510

Asn Pro Asp Ser Ser Ile Asn Pro Asp His Leu Ser Tyr Phe His Phe
        515                 520                 525
```

```
Val Gly Arg Ile Met Gly Leu Ala Val Phe His Gly His Tyr Ile Asn
    530                 535                 540

Gly Gly Phe Thr Val Pro Phe Tyr Lys Gln Leu Leu Gly Lys Pro Ile
545                 550                 555                 560

Gln Leu Ser Asp Leu Glu Ser Val Asp Pro Glu Leu His Lys Ser Leu
                565                 570                 575

Val Trp Ile Leu Glu Asn Asp Ile Thr Pro Val Leu Asp His Thr Phe
                580                 585                 590

Cys Val Glu His Asn Ala Phe Gly Arg Ile Leu Gln His Glu Leu Lys
                595                 600                 605

Pro Asn Gly Arg Asn Val Pro Val Thr Glu Glu Asn Lys Lys Glu Tyr
    610                 615                 620

Val Arg Leu Tyr Val Asn Trp Arg Phe Met Arg Gly Ile Glu Ala Gln
625                 630                 635                 640

Phe Leu Ala Leu Gln Lys Gly Phe Asn Glu Leu Ile Pro Gln His Leu
                645                 650                 655

Leu Lys Pro Phe Asp Gln Lys Glu Leu Glu Leu Ile Ile Gly Gly Leu
                660                 665                 670

Asp Lys Ile Asp Leu Asn Asp Trp Lys Ser Asn Thr Arg Leu Lys His
                675                 680                 685

Cys Val Ala Asp Ser Asn Ile Val Arg Trp Phe Trp Gln Ala Val Glu
    690                 695                 700

Thr Phe Asp Glu Glu Arg Arg Ala Arg Leu Leu Gln Phe Val Thr Gly
705                 710                 715                 720

Ser Thr Arg Val Pro Leu Gln Gly Phe Lys Ala Leu Gln Gly Ser Thr
                725                 730                 735

Gly Ala Ala Gly Pro Arg Leu Phe Thr Ile His Leu Ile Asp Ala Asn
    740                 745                 750

Thr Asp Asn Leu Pro Lys Ala His Thr Cys Phe Asn Arg Ile Asp Ile
                755                 760                 765

Pro Pro Tyr Glu Ser Tyr Glu Lys Leu Tyr Glu Lys Leu Leu Thr Ala
    770                 775                 780

Val Glu Glu Thr Cys Gly Phe Ala Val Glu
785                 790

<210> SEQ ID NO 31
<211> LENGTH: 465
<212> TYPE: PRT
<213> ORGANISM: Homo sapiens
<220> FEATURE:
<221> NAME/KEY: MOD_RES
<222> LOCATION: (193)
<223> OTHER INFORMATION: Variable amino acid
<220> FEATURE:
<221> NAME/KEY: MOD_RES
<222> LOCATION: (198)
<223> OTHER INFORMATION: Variable amino acid

<400> SEQUENCE: 31

Met Thr Ser Met Ala Ser Leu Phe Ser Phe Thr Ser Pro Ala Val Lys
1               5                   10                  15

Arg Leu Leu Gly Trp Lys Gln Gly Asp Glu Glu Glu Lys Trp Ala Glu
                20                  25                  30

Lys Ala Val Asp Ala Leu Val Lys Lys Leu Lys Lys Lys Lys Gly Ala
                35                  40                  45

Met Glu Glu Leu Glu Lys Ala Leu Ser Ser Pro Gly Gln Pro Ser Lys
    50                  55                  60
```

-continued

```
Cys Val Thr Ile Pro Arg Ser Leu Asp Gly Arg Leu Gln Val Ser His
 65                  70                  75                  80

Arg Lys Gly Leu Pro His Val Ile Tyr Cys Arg Val Trp Arg Trp Pro
                 85                  90                  95

Asp Leu Gln Ser His His Glu Leu Lys Pro Leu Asp Ile Cys Glu Phe
                100                 105                 110

Pro Phe Gly Ser Lys Gln Lys Glu Val Cys Ile Asn Pro Tyr His Tyr
            115                 120                 125

Lys Arg Val Glu Ser Pro Val Leu Pro Pro Val Leu Val Pro Arg His
130                 135                 140

Asn Glu Phe Asn Pro Gln His Ser Leu Leu Val Gln Phe Arg Asn Leu
145                 150                 155                 160

Ser His Asn Glu Pro His Met Pro Gln Asn Ala Thr Phe Pro Asp Ser
                165                 170                 175

Phe His Gln Pro Asn Asn Thr Pro Phe Pro Leu Ser Pro Asn Ser Pro
            180                 185                 190

Xaa Pro Pro Ser Pro Xaa Ser Ser Thr Tyr Pro Asn Ser Pro Ala Ser
        195                 200                 205

Ser Gly Pro Gly Ser Pro Phe Gln Leu Pro Ala Asp Thr Pro Pro Pro
210                 215                 220

Ala Tyr Met Pro Pro Asp Asp Gln Met Gly Gln Asp Asn Ser Gln Pro
225                 230                 235                 240

Met Asp Thr Ser Asn Asn Met Ile Pro Gln Ile Met Pro Ser Ile Ser
                245                 250                 255

Ser Arg Asp Val Gln Pro Val Ala Tyr Glu Glu Pro Lys His Trp Cys
                260                 265                 270

Ser Ile Val Tyr Tyr Glu Leu Asn Asn Arg Val Gly Glu Ala Phe His
            275                 280                 285

Ala Ser Ser Thr Ser Val Leu Val Asp Gly Phe Thr Asp Pro Ser Asn
290                 295                 300

Asn Lys Ser Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
            340                 345                 350

Ile Phe Val Gln Ser Arg Asn Cys Asn Phe His His Gly Phe His Pro
            355                 360                 365

Thr Thr Val Cys Lys Ile Pro Ser Ser Cys Ser Leu Lys Ile Phe Asn
370                 375                 380

Asn Gln Glu Phe Ala Gln Leu Leu Ala Gln Ser Val Asn His Gly Phe
385                 390                 395                 400

Glu Ala Val Tyr Glu Leu Thr Lys Met Cys Thr Ile Arg Met Ser Phe
                405                 410                 415

Val Lys Gly Trp Gly Ala Glu Tyr His Arg Gln Asp Val Thr Ser Thr
            420                 425                 430

Pro Cys Trp Ile Glu Ile His Leu His Gly Pro Leu Gln Trp Leu Asp
            435                 440                 445

Lys Val Leu Thr Gln Met Gly Ser Pro Leu Asn Pro Ile Ser Ser Val
450                 455                 460

Ser
465
```

<210> SEQ ID NO 32
<211> LENGTH: 465
<212> TYPE: PRT
<213> ORGANISM: Homo sapiens

<400> SEQUENCE: 32

Met Asn Val Thr Ser Leu Phe Ser Phe Thr Ser Pro Ala Val Lys Arg
 1               5                  10                  15

Leu Leu Gly Trp Lys Gln Gly Asp Glu Glu Lys Trp Ala Glu Lys
             20                  25                  30

Ala Val Asp Ala Leu Val Lys Lys Leu Lys Lys Lys Gly Ala Met
         35                  40                  45

Glu Glu Leu Glu Lys Ala Leu Ser Cys Pro Gly Gln Pro Ser Asn Cys
 50                  55                  60

Val Thr Ile Pro Arg Ser Leu Asp Gly Arg Leu Gln Val Ser His Arg
 65                  70                  75                  80

Lys Gly Leu Pro His Val Ile Tyr Cys Arg Val Trp Arg Trp Pro Asp
                 85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr Lys
        115                 120                 125

Arg Val Glu Ser Pro Val Leu Pro Pro Val Leu Val Pro Arg His Ser
130                 135                 140

Glu Tyr Asn Pro Gln His Ser Leu Leu Ala Gln Phe Arg Asn Leu Gly
145                 150                 155                 160

Gln Asn Glu Pro His Met Pro Leu Asn Ala Thr Phe Pro Asp Ser Phe
                165                 170                 175

Gln Gln Pro Asn Ser His Pro Phe Pro His Ser Pro Asn Ser Ser Tyr
            180                 185                 190

Pro Asn Ser Pro Gly Ser Ser Ser Thr Tyr Pro His Ser Pro Thr
        195                 200                 205

Ser Ser Asp Pro Gly Ser Pro Phe Gln Met Pro Ala Asp Thr Pro Pro
210                 215                 220

Pro Ala Tyr Leu Pro Pro Glu Asp Pro Met Thr Gln Asp Gly Ser Gln
225                 230                 235                 240

Pro Met Asp Thr Asn Met Met Ala Pro Pro Leu Pro Ser Glu Ile Asn
                245                 250                 255

Arg Gly Asp Val Gln Ala Val Ala Tyr Glu Glu Pro Lys His Trp Cys
            260                 265                 270

Ser Ile Val Tyr Tyr Glu Leu Asn Asn Arg Val Gly Glu Ala Phe His
        275                 280                 285

Ala Ser Ser Thr Ser Val Leu Val Asp Gly Phe Thr Asp Pro Ser Asn
290                 295                 300

Asn Lys Asn Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
            340                 345                 350

Ile Phe Val Gln Ser Arg Asn Cys Asn Tyr His His Gly Phe His Pro
        355                 360                 365

Thr Thr Val Cys Lys Ile Pro Ser Gly Cys Ser Leu Lys Ile Phe Asn
370                 375                 380

```
Asn Gln Glu Phe Ala Gln Leu Leu Ala Gln Ser Val Asn His Gly Phe
385                 390                 395                 400

Glu Thr Val Tyr Glu Leu Thr Lys Met Cys Thr Ile Arg Met Ser Phe
            405                 410                 415

Val Lys Gly Trp Gly Ala Glu Tyr His Arg Gln Asp Val Thr Ser Thr
        420                 425                 430

Pro Cys Trp Ile Glu Ile His Leu His Gly Pro Leu Gln Trp Leu Asp
    435                 440                 445

Lys Val Leu Thr Gln Met Gly Ser Pro His Asn Pro Ile Ser Ser Val
    450                 455                 460

Ser
465

<210> SEQ ID NO 33
<211> LENGTH: 5
<212> TYPE: PRT
<213> ORGANISM: Homo sapiens

<400> SEQUENCE: 33

Pro Pro Pro Ala Tyr
  1               5

<210> SEQ ID NO 34
<211> LENGTH: 5
<212> TYPE: PRT
<213> ORGANISM: Homo sapiens

<400> SEQUENCE: 34

Pro Pro Pro Ala Tyr
  1               5

<210> SEQ ID NO 35
<211> LENGTH: 1644
<212> TYPE: DNA
<213> ORGANISM: Homo sapiens

<400> SEQUENCE: 35
atggattcct tcaaggtagt gctggagggg ccagcacctt ggggcttccg gctgcaaggg     60
ggcaaggact tcaatgtgcc cctctccatt tcccggctca ctcctggggg caaagcggcg    120
caggccggag tggccgtggg tgactgggtg ctgagcatcg atggcgagaa tgcgggtagc    180
ctcacacaca tcgaagctca gaacaagatc cgggcctgcg gggagcgcct cagcctgggc    240
ctcagcaggg cccagccggt tcagagcaaa ccgcagaagg cctccgcccc cgccgcggac    300
cctccgcggt acacctttgc acccagcgtc tccctcaaca agacggcccg gccctttggg    360 gcgccccgc cgctgacag cgccccgcaa cagaatggac agccgctccg accgctggtc    420
ccagatgcca gcaagcagcg gctgatggag aacacagagg actggcggcc gcggccgggg    480
acaggccagt cgcgttcctt ccgcatcctt gcccacctca ggcaccga gttcatgcaa    540 gacccggatg aggagcacct gaagaaatca agccaggtgc caggacaga gccccagcc    600 ccagcctcat ctacacccca ggagccctgg cctggcccta ccgccccag ccctaccagc    660 cgcccgccct gggctgtgga ccctgcgttt gccgagcgct atgccccgga caaaacgagc    720
acagtgctga cccggcacag ccagccggcc acgcccacgc cgctgcagag ccgcacctcc    780
attgtgcagg cagctgccgg aggggtgcca ggagggggca gcaacaacgg caagactccc    840
gtgtgtcacc agtgccacaa ggtcatccgg ggccgctacc tggtggcgtt gggcacgcg    900 taccacccgg aggagtttgt gtgtagccag tgtgggaagg tcctggaaga gggtggcttc    960
```

-continued

| | |
|---|---|
| tttgaggaga agggcgccat cttctgccca ccatgctatg acgtgcgcta tgcacccagc | 1020 |
| tgtgccaagt gcaagaagaa gattacaggc gagatcatgc acgccctgaa gatgacctgg | 1080 |
| cacgtgcact gctttacctg tgctgcctgc aagacgccca tccggaacag ggccttctac | 1140 |
| atggaggagg gcgtgcccta ttgcgagcga gactatgaga agatgtttgg cacgaaatgc | 1200 |
| catggctgtg acttcaagat cgacgctggg accgcttcc tggaggccct gggcttcagc | 1260 |
| tggcatgaca cctgcttcgt ctgtgcgata tgtcagatca acctggaagg aaagaccttc | 1320 |
| tactccaaga aggacaggcc tctctgcaag agccatgcct tctctcatgt gtgagcccct | 1380 |
| tctgcccaca gctgccgcgg tggcccctag cctgaggggc ctggagtcgt ggccctgcat | 1440 |
| ttctgggtag ggctggcaat ggttgcctta accctggctc ctggcccgag cctgggctcc | 1500 |
| cgggcccctg cccacccacc ttatcctccc accccactcc ctccaccacc acagcacacc | 1560 |
| ggtgctggcc acaccagccc cctttcacct ccagtgccac aataaacctg tacccagctg | 1620 |
| aattccaaaa aatccaaaaa aaaa | 1644 |

<210> SEQ ID NO 36
<211> LENGTH: 1665
<212> TYPE: DNA
<213> ORGANISM: Homo sapiens

<400> SEQUENCE: 36

| | |
|---|---|
| cgacgcagag cagcgccctg gccgggccaa gcaggagccg gcatcatgga ttccttcaag | 60 |
| gtagtgctgg aggggccagc accttggggc ttccggctgc aagggggcaa ggacttcaat | 120 |
| gtgcccctct ccatttcccg gctcactcct gggggcaaag cggcgcaggc cggagtggcc | 180 |
| gtgggtgact gggtgctgag catcgatggc gagaatgcgg gtagcctcac acacatcgaa | 240 |
| gctcagaaca agatccgggc ctgcggggag cgcctcagcc tgggcctcag cagggcccag | 300 |
| ccggttcaga gcaaaccgca gaaggcctcc gcccccgccg cggaccctcc gcggtacacc | 360 |
| tttgcaccca cgtctcccct caacaagacg gcccggccct ttggggcgcc ccgcccgct | 420 |
| gacagcgccc cgcaacagaa tggacagccg ctccgaccgc tggtcccaga tgccagcaag | 480 |
| cagcggctga tggagaacac agaggactgg cggccgcggc cggggacagg ccagtcgcgt | 540 |
| tccttccgca tccttgccca cctcacaggc accgagttca tgcaagaccc ggatgaggag | 600 |
| cacctgaaga aatcaagcca ggtgcccagg acagaagccc cagccccagc ctcatctaca | 660 |
| ccccaggagc cctggcctgg ccctaccgcc ccagcccta ccagccgccc gccctgagct | 720 |
| gtggaccctg cgtttgccga gcgctatgcc ccggacaaaa cgagcacagt gctgacccgg | 780 |
| cacagccagc cggccacgcc cacgccgctg cagagccgca cctccattgt gcaggcagct | 840 |
| gccggagggg tgccaggagg gggcagcaac aacggcaaga ctcccgtgtg tcaccagtgc | 900 |
| cacaaggtca tccggggccg ctacctggtg gcgttgggcc acgcgtacca cccggaggag | 960 |
| tttgtgtgta gccagtgtgg aaggtcctg aagagggtg gcttctttga ggagaagggc | 1020 |
| gccatcttct gccaccatg ctatgacgtg cgctatgcac ccagctgtgc caagtgcaag | 1080 |
| aagaagatta caggcgagat catgcacgcc ctgaagatga cctggcacgt gcactgcttt | 1140 |
| acctgtgctg cctgcaagac gcccatccgg aacaggcct tctacatgga ggagggcgtg | 1200 |
| ccctattgcg agcgagacta tgagaagatg tttggcacga atgccatgg ctgtgacttc | 1260 |
| aagatcgacg ctggggaccg cttcctggag gccctgggct tcagctggca tgacacctgc | 1320 |
| ttcgtctgtg cgatatgtca gatcaacctg gaaggaaaga ccttctactc caagaaggac | 1380 |

-continued

| | | |
|---|---|---|
| aggcctctct gcaagagcca tgccttctct catgtgtgag ccccttctgc ccacagctgc | 1440 |
| cgcggtggcc cctagcctga ggggcctgga gtcgtggccc tgcatttctg ggtagggctg | 1500 |
| gcaatggttg ccttaaccct ggctcctggc ccgagcctgg gctcccgggc ccctgcccac | 1560 |
| ccaccttatc ctcccacccc actccctcca ccaccacagc acaccggtgc tggccacacc | 1620 |
| agccccnttt cacctccagt gccacaataa acctgtaccc agctg | 1665 |

<210> SEQ ID NO 37
<211> LENGTH: 3056
<212> TYPE: DNA
<213> ORGANISM: Homo sapiens

<400> SEQUENCE: 37

| | | |
|---|---|---|
| ggcagctgag gagtggaggc tgggcagctc cgactccctg acgccagcgc gaccagatca | 60 |
| atccaggctc caggagaaag caggcgggcg ggcggagaaa ggagaggccg agcggctcaa | 120 |
| cccgggccga ggctcgggga gcggagagtg gcgcagcgcc cggccgtccg gacccgggcc | 180 |
| gcgagacccc gctcgcccgg ccactcgtgc tcccacacgg acgggcgcgc cgccaacccg | 240 |
| gtgctgactg ggttactttt ttaaacacta ggaatggtaa tttctactct tctggacttc | 300 |
| aaactaagaa gttaaagaga cttctctgta aataaacaaa tctcttctgc tgtccttttg | 360 |
| catttggaga cagcttattt tcaccatatc caaggagtat aactagtgct gtcattatga | 420 |
| atgtgacaag tttatttttcc tttacaagtc cagctgtgaa gagacttctt gggtggaaac | 480 |
| agggcgatga agaagaaaaa tgggcagaga agctgttga tgctttggtg aaaaaactga | 540 |
| agaaaaagaa aggtgccatg gaggaactgg aaaaggcctt gagctgccca gggcaaccga | 600 |
| gtaactgtgt caccattccc cgctctctgg atggcaggct gcaagtctcc caccggaagg | 660 |
| gactgcctca tgtcatttac tgccgtgtgt ggcgctggcc cgatcttcag agccaccatg | 720 |
| aactaaaacc actggaatgc tgtgagtttc cttttggttc caagcagaag gaggtctgca | 780 |
| tcaatcccta ccactataag agagtagaaa gccctgtact tcctcctgtg ctggttccaa | 840 |
| gacacagcga atataatcct cagcacagcc tcttagctca gttccgtaac ttaggacaaa | 900 |
| atgagcctca catgccactc aacgccactt ttccagattc tttccagcaa cccaacagcc | 960 |
| acccgtttcc tcactctccc aatagcagtt acccaaactc tcctgggagc agcagcagca | 1020 |
| cctaccctca ctctcccacc agctcagacc caggaagccc tttccagatg ccagctgata | 1080 |
| cgccccacc tgcttacctg cctcctgaag accccatgac ccaggatggc tctcagccga | 1140 |
| tggacacaaa catgatggcg cctcccctgc cctcagaaat caacagagga gatgttcagg | 1200 |
| cggttgctta tgaggaacca aaacactggt gctctattgt ctactatgag ctcaacaatc | 1260 |
| gtgtgggtga agcgttccat gcctcctcca caagtgtgtt ggtggatggt ttcactgatc | 1320 |
| cttccaacaa taagaaccgt ttctgccttg ggctgctctc caatgttaac cggaattcca | 1380 |
| ctattgaaaa caccaggcgg catattggaa aaggagttca tctttattat gttggagggg | 1440 |
| aggtgtatgc cgaatgcctt agtgacagta gcatctttgt gcaaagtcgg aactgcaact | 1500 |
| accatcatgg atttcatcct actactgttt gcaagatccc tagtgggtgt agtctgaaaa | 1560 |
| tttttaacaa ccaagaattt gctcagttat tggcacagtc tgtgaaccat ggatttgaga | 1620 |
| cagtctatga gcttacaaaa atgtgtacta tacgtatgag ctttgtgaag ggctgggag | 1680 |
| cagaatacca ccgccaggat gttactagca cccctgctg gattgagata catctgcacg | 1740 |
| gccccctcca gtggctggat aaagttctta ctcaaatggg ttcacctcat aatcctattt | 1800 |
| catctgtatc ttaaatggcc ccaggcatct gcctctggaa aactattgag ccttgcatgt | 1860 |

-continued

| | |
|---|---|
| acttgaagga tggatgagtc agacacgatt gagaactgac aaaggagcct tgataatact | 1920 |
| tgacctctgt gaccaactgt tggattcaga aatttaaaca aaaaaaaaaa aaaacacaca | 1980 |
| caccttggta acatactgtt gatatcaaga acctgtttag tttacattgt aacattctat | 2040 |
| tgtaaaatca actaaaattc agacttttag caggactttg tgtacagtta aaggagagat | 2100 |
| ggccaagcca gggacaaatt gtctattaga aaacggtcct aagagattct ttggtgtttg | 2160 |
| gcactttaag gtcatcgttg ggcagaagtt tagcattaat agttgttctg aaacgtgttt | 2220 |
| tatcaggttt agagcccatg ttgagtcttc ttttcatggg ttttcataat attttaaaac | 2280 |
| tatttgttta gcgatggttt tgttcgttta agtaaaggtt aatcttgatg atatacataa | 2340 |
| taatctttct aaaattgtat gctgaccata cttgctgtca gaataatgct aggcatatgc | 2400 |
| tttttgctaa atatgtatgt acagagtatt tggaagttaa gaattgatta gactagtgaa | 2460 |
| tttaggagta tttgaggtgg gtgggggaa gagggaaatg acaactgcaa atgtagacta | 2520 |
| tactgtaaaa attcagtttg ttgctttaaa gaaacaaact gatacctgaa ttttgctgtg | 2580 |
| tttccatttt ttagagattt ttatcatttt tttctctctc ggcattcttt tttctcatac | 2640 |
| tcttcaaaaa gcagttctgc agctggttaa ttcatgtaac tgtgagagca aatgaataat | 2700 |
| tcctgctatt ctgaaattgc ctacatgttt caataccagt tatatggagt gcttgaattt | 2760 |
| aataagcagt ttttacggag tttacagtac agaaataggc tttaattttc aagtgaattt | 2820 |
| tttgccaaac ttagtaactc tgttaaatat tggaggatt taaagaacat cccagtttga | 2880 |
| attcatttca aactttttaa attttttgt actatgtttg gttttatttt ccttctgtta | 2940 |
| atcttttgta ttcacttatg ctctcgtaca ttgagtactt ttattccaaa actagtgggt | 3000 |
| tttctctact ggaaattttc aataaacctg tcattattgc ttactttgat taaaaa | 3056 |

<210> SEQ ID NO 38
<211> LENGTH: 7012
<212> TYPE: DNA
<213> ORGANISM: Homo sapiens

<400> SEQUENCE: 38

| | |
|---|---|
| ccgggtcctg ggcgagcggg cgccgtgcgc gtgtcccgcg gccgagctgc taataaagtt | 60 |
| gcagcgagga gaagcgcagc gacggcgtcg ggagagcgcg cctagccggc tcgcgaaaag | 120 |
| gaagctgttg aagttattga agtacctgtt gctatattct aagaaattaa aatgtccaga | 180 |
| aatctgcctc tgacttgacc caatgaaaga agcatatggc acttgtgaag ataaatgtta | 240 |
| ctcctccctt tttaattgga acttctgctt aggacctgtg tatgacgttt cacctgtgat | 300 |
| ctgttctttc ggtagccact gactttgagt tacaggaagg tctccgaaga tttgtgtcaa | 360 |
| atgacgtcaa tggccagctt gttttctttt actagtccag cagtaaagcg attgttgggc | 420 |
| tggaaacaag gtgatgagga ggagaaatgg gcagaaaagg cagttgatgc tttggtgaag | 480 |
| aaactaaaaa agaaaaaggg tgccatggag gaactggaga aagccttgag cagtccagga | 540 |
| cagccgagta aatgtgtcac tattcccaga tctttagatg gacgcctgca ggtttctcac | 600 |
| agaaaaggct taccccatgt tatatattgt cgtgtttggc gctggccgga tttgcagagt | 660 |
| catcatgagc taaagccgtt ggatatttgt gaatttcctt ttggatctaa gcaaaaagaa | 720 |
| gtttgtatca acccatacca ctataagaga gtggagagtc cagtcttacc tccagtatta | 780 |
| gtgcctcgtc ataatgaatt caatcccaca cacagcctttc tggttcagtt taggaacctg | 840 |
| agccacaatg aaccacacat gccacaaaat gccacgtttc cagattcttt ccaccagccc | 900 |

```
aacaacactc cttttccctt atctccaaac agcccttatc cccttctcc tgctagcagc      960 acatatccca actccccagc aagttctgga ccaggaagtc catttcagct cccagctgat     1020
acgcctcctc ctgcctatat gccacctgat gatcagatgg gtcaagataa ttcccagcct    1080
atggatacaa gcaataatat gattcctcag attatgccca gtatatccag cagggatgtt    1140
cagcctgttg cctatgaaga gcctaaacat tggtgttcaa tagtctacta tgaattaaac    1200
aatcgtgttg gagaagcttt tcatgcatct tctactagtg tgttagtaga tggattcaca    1260
gatccttcaa ataacaaaag tagattctgc ttgggtttgt tgtcaaatgt taatcgtaat    1320
tcgacaattg aaaacactag gcgacatatt ggaaaaggtg ttcatctgta ctatgttggt    1380
ggagaggtgt atgcggaatg cctcagtgac agcagcatat ttgtacagag taggaactgc    1440
aactttcatc atggctttca tcccaccact gtctgtaaga ttcccagcag ctgcagcctc    1500
aaaattttta acaatcagga gtttgctcag cttctggctc aatctgtcaa ccatgggttt    1560
gaggcagtat atgagctcac caaaatgtgt accattcgga tgagttttgt caagggttgg    1620
ggagcagaat atcaccggca ggatgtaacc agcaccccat gttggattga gattcatctt    1680
catgggcctc ttcagtggct ggataaagtc cttactcaga tgggctcccc tctgaaccc     1740 atatcttctg tttcataatg cagaagtatt cttttcaatt atattgttag tggacttgtt    1800
ttaattttag agaactttg agtacagata ctgtgagctt acattgaaaa cagatattac     1860
agcttatttt tttctacata attgtgacca atacatttgt attttgtgat gaatctacat    1920
ttgtttgtat tcatgttcat gtgattaact cttagaagtg ttgtaaaaga tgcagagtaa    1980
gtattatgcc ccagttcaga aatttggcat tgatcttaaa ctggaacatg cttttacttt    2040
attgccctaa caatttttta ttaaatttat ttgaaaatgc atcacatgat gaaaaattat    2100
agtagcttat aagagggcat atacagtgaa gagtaagttt tccctcctac tctcgatctt    2160
ccagaagctg tacttttacc agtttctttg tcccaccaac ttaaaaaaaa aaagtacaat    2220
tcattgtttt gcaaaagtgt atggtagggg cttaaaagaa actataaagt tttatttgaa    2280
tgaacactat gcactgctgt aactggtagt gttcagtaaa agcaaaatga tagttttcta    2340
gatgacataa aatttacatt taatacagat aagtgttctt cagtgtaatg tgacttcatg    2400
ctatatatct tttgtaagac atttcctttt ttaaaaaaat ttttgcaaat aactgatctc    2460
aagtatatgt catttactca aaatctgtca taagcattac tttatagcta gtgacagtgc    2520
atgcacagcc ttgttcaact atgtttgctg cttttggaca atgttgcaag aactctattt    2580
ttgacatgca ttaatctttt attttgcact tttatgggtg acagttttta gcataacctt    2640
tgataaaata cactcaagtg acttggactt agatgcttat ccttacgtcc ttggtacctt    2700
ttttgtatta acaaacactg caattatag attacatttg taggaagtta tgcttttttc     2760 tggttttgt tttactttca acctaggtta taagactgtt attctatagc tccaacttaa     2820
ggtgcctttt taattcccta cagttttatg ggtgttatca gtgctggaga atcatgtagt    2880
taatcccatt gctcttacaa gtgtcagctt acttgtatca gcctccctac gcaaggacct    2940
atgcactgga gccgtaggag gctcttcagt tgggccccaa ggataaggct actgatttga    3000
tactaaatga atcagcagtg gatgtaggga tagctgattt taaaacactc ggctgggcac    3060
agtggctcac acctgtaatc ccagcacttt gggaggctga ggcaggcaga tcatgatgtc    3120
aggagtttga gaccagcctg gccaatatgg tgaaaccctg tctctacaaa aaatacaaaa    3180
attagctggg catggtggtg cgtgcctgaa gtcccagcta ctcgggaagc tgaggcagaa    3240
gaatcacttg aacctgggag gcggaggttg tggtgagccg agatcgcacc actgcactcc    3300
```

```
agcctgggcg acagagcgag actctgcctc aaaaaacaaa acaaaacaaa acactcaccc    3360
atcaacgaat atagactctt ctctcattta tcgatgatcc tcttttttcca ttttttaagt   3420 acttatgtgg aagctagtct cccaaaacac aatctttaga gagaaaagac atgaacgaac    3480
tccaaaatat ccatttaatc aatcatgttt ttggctttgg ataaagaact ttgaaccagt   3540 tttttttctca ggagctgtca aatggacact taattatgac atgagaatga agaaattatt  3600
ttggaaaaaa aaaatgacct aatttaccta tcagtgaaag ctttatttc tggtgccttt    3660 tgaaagtata tggagtcata tcattcttct gtttaaaatg ttagtttggt ttgactttcc   3720
actttgtcct ttctgctctt gtgaagaaaa aaaaagcat tttcgaggaa agaattatgc    3780
aatttctttt gttttctgtg tcattattta ttgcttttc aatgtgcagc cagtggatgg    3840
ttttagttct ttcagatgaa ctgccatttg tgtttcagct cacagttctt tgctgggtaa   3900
aagaaatact ttctgacagt cacctgagcc ttaaatgtaa gtattacatg acatgcattc   3960
tgtttcttcc agagttctgt ctgccacacg aaagagaata tttgcttact tgatagaact   4020
ttggcatttt catcattctt ttacttaacc aggcttatgg catgatctct ggaacaaatt   4080
tgtaggaaaa aattactcca attgaatgac tgatgtatgt aatcaacttc attgggctgc   4140
agtaaactag tggaaattag agagttgttt tattggtgtt ttctactgtg agttaattaa   4200
aaattgtttt tatttggggt cattatgtca cagtcttgag ttaacaagat cttacgtgat   4260 tggcctttc tttgttttct cttaggagtt gtgtctcatg aatgacagta ctaaagctat   4320
taacaactaa gagtttgaca gagaactata agcctgttgt atctcctaaa agttgtcaac   4380
tccccaccct tggactttaa atgaaaattt tattcagtcc agctattctt acagtcccta   4440
aggattttca tatatctatg tataggagat aaaatttgct agtaagattt ttaaaaactg   4500
gctagtgaaa ggaaagtacc tctgaaagaa accattttag caaattatgg ttatatgttt   4560
taatttaatc tacagaatgt tttatagtaa aattctagca ccactagaat aatcacatag   4620
catgtacaat atatttatgc tggctgaaaa gacagaatct gggaataata aaattgcaac   4680
cagtttggta atgcaaacag cagaatagaa tgaaatctca gtaatgaatt aaagcaacaa   4740
aaagatattg attggcaaaa agcaagatat aagagattca tttgcttaac atttctacat   4800
aatatttatg gtctggtcag tattggtctg gtcagtattg cctggctgac gtgaaatgta   4860
aactagtagg cgtgttattg atctgctaaa actaaccctc ttttttaagag gagatttaag   4920 gaagacgtca atcaaaatgt caaatatgtg tgtcagaata taaataattt ttcacattgt   4980
attgttgcta tataaaaaaa ataatagaat tggttgggtt tctgaggtga aatccagagt   5040
aagagtacta gacagttcaa caagccacat ctaatggcac agatagagga tgtagctatt   5100 ttatacctt cataacattt gagagtaaga tatccttcag gatgtgaagt gattattaag    5160
tactcatacc tgaaatctgt tgtcaagatt agaactgggg ttcatgttaa aaaccttcca   5220
tattacctga gggtacctgt ggggaacagt tccttcccct gtgtggtagt attttgttgg   5280
aagagaatgt ttatacaaaa aatgaaattc ttccaacagc agagaaactc taaaaagttt   5340
gatagtacct atcaaagtgc tgtacttctg tgatagagaa catctgatgt accaatttag   5400
atctatttct ttatactttt tctaatcaat tgcttaatag tactttggat gattatcacc   5460
tttgccactt aaaatatata aatatccttt ttacttcatg aggaaggaag aatttttga    5520 taattactga gttcagcctt ttgtgatgac ttatattttg gacttacatt ttaactttaa   5580
agaatgtcag atcccttctt tgtcttacta gttaaatcct cacctaatct cttgggtatg   5640
```

```
aatataaatg tgtgtcatcg ttatattgtt cagctagatg agcaagtatc ttagggtagt      5700
aggtagcctg gtggttttag aagtgtttgg tgattttat ggagagagtt ttcctaagtg       5760
gtggtttata ggtggtatca gatattatta gggcagcttt ttggggagta atctcaggtc      5820
tcccagagca gcagcatttt tctcattgat ataagtaaga ttcttaggag cttttcttat     5880
cacacaagat gcctgaatcg aatgtgagaa ttgaaggcat ttcttctgca taaacaaaga     5940
attctacctg ctggacagaa acctggaaag ttctttggaa ttcgctgaat tacagtttag     6000
tatgtcctga ttacagagtg acaatattta tcaagccttt gttatattgg attatcttct     6060
ctcttaaaat acaactgtat tataattgaa atgcagccc aaaattggat ggtttaccaa      6120
aaccaatgaa agggatttca cacatcaatt tttatttctg ttttgaagag cacatgctat     6180
ataataattg ctagtagcaa ctgcagtaaa acaggtgata agttatttc tctgaaaaga      6240 tccagtccta gagcaggatt cttcgatcat tcatggcaga gtgaaaaagg tttgtatggt     6300
tcttgtccaa ataactcagt tcttaaaatt cttaaaatga tcgtaaacca ttatccttta     6360
aaggtttatt tgaagatgct gttaaagtac agaattttgt gtacaggtag attttttccgt   6420 ccctcattaa tagtgccttc ttaattaata cagactggtg ttagctataa caaaactcca    6480
gtaaggccaa agaatcccaa gttctttgtg gaaaaaaaaa aaaaatcttt tagggtcaga    6540
ttttcccttc taatatcatt gaagatgatg ttgcattgat ttattcataa agtattttaa    6600
ctataggaac tctagaagat aatggttagg caagtgattt ttttttttaaa tatggttggc    6660 gtaagttgta ttttgaaatt cacttatttt aaaatcgaag aggattgtaa tcatggaaat     6720
agaatgtttg tatctacctg cccacatttt cttaaaaga tatttcatat acagataatg     6780
aagaccaagc tagtggctgc actgtaggtc tgctgcttat ttgtatttgt tgtgcttctg    6840
tttatgttgt agaagctgaa attctagcaa catgcttcaa ttctgttatt ttgatactta    6900
tgaaaatgta ttaggtttta ctatattgtg cttttgaaag ccataactct taagaacttt    6960 gttttttgcat attgtttgct aattctttac tttaataaac ctcaaaaccct gc          7012

<210> SEQ ID NO 39
<211> LENGTH: 5333
<212> TYPE: DNA
<213> ORGANISM: Homo sapiens

<400> SEQUENCE: 39
ggaagcagcg agggcggcgg gcgtccggct gcgagcgcgg cggctcccggg ctgggccagc      60 caggggcggc tcctggcggc ggcgcggccg agcgctcggt tctacggttc cagcccgtgg     120
tctccggccc aacgcctgcg ccgcgcactc ggcgtcccgg ctcggacccc ggcgcccagc     180
ccgtggccgt aaccttgagg cggcggcggg gccgggccgg gccgggctgg ggggcggcgg    240
cactggatcc gaggccggcc ggccgctggc gggagatgtc gaaccccggg acccgtagga    300
acggctccag catcaagatc cgtctgacag tattgtgtgc caagaacctt gcaaagaaag    360
acttcttcag actccccgac cccttttgcca agattgttgt ggacggctct gggcagtgcc    420
actcaaccga cactgtgaaa aacacccctgg acccaaagtg gaaccagcac tatgacctgt    480
atgttgggaa aacggactcg ataaccatca gtgtgtggaa ccacaagaag atccacaaga    540
agcagggggc tggcttcctg ggctgtgtgc ggctgctctc caatgccatc agcagattga    600
aagacactgg ctaccagcgt ttggatctat gcaaactaaa tccctcagat actgatgcag    660
ttcgtggcca aatagtggtc agtttacaga cccgagacaa ataggcggt ggagggtcag     720 tggtggactg cagagggctg ctggagaacg aaggaacagt gtatgaagac tcaggccctg    780
```

-continued

```
gaaggccgct cagctgcctc atggaggaac ctgccccata tacagatggt actggtgcag      840
cagcaggagg cgggaactgc aggtttgtgg agtctccaag ccaagatcag agactcctgg      900
tacagcgact ccgaaatcct gaggttcgag ggcccttaca dacacccag aaccgaccac       960
atggccacca gtcgccagag ctgcctgaag gctatgagca aggacaaca gtgcagggac      1020
aagtttactt tttgcacacg cagactggag tcagtacatg gcatgacccc aggatcccca     1080
gagaccttaa cagtgtgaac tgcgatgaac ttgggccact gcctccaggc tgggaagtcc     1140
gaagcacagt gtcgggaaga atctattttg tagatcacaa taataggaca acccagttta    1200
cagatccacg gcttcaccac atcatgaatc accagtgcca actcaaggag cccagccagc    1260
cgctgcagct gcccagtgag ggctccgtgg aggacgagga gcttcctgcc cagagatatg    1320
agagggactt agtccagaag ctcaaagttc tcaggcacga gctctctctt cagcagcccc    1380
aggctggtca ctgtcgaata gaagtctcca gagaagagat atttgaggag tcgtatcgcc    1440
agatcatgaa gatgcggcca aaagacctaa agaagcgcct gatggtgaag ttccgagggg    1500
aggaaggttt ggactatggt ggagtggctc gggagtggct gtatttgttg tgccatgaaa    1560
tgttgaaccc gtactatgga ctcttccagt attccacgga caatatttac acactgcaga    1620
tcaacccaga ttcttctatc aaccctgacc atctgtcata cttccacttt gtgggtcgca    1680
tcatgggtct ggctgtgttc cacggacact acataaatgg gggtttcaca gttccgttct    1740
acaagcagct cctggggaag ccaatccagc tgtcggacct ggagtccgtg gacccagaac    1800
tgcataagag cttggtgtgg attctagaga atgcatcac gcctgtgttg gatcatacct     1860
tctgcgtgga gcacaacgct ttcgggcgga ttctccagca tgaactgaaa cccaatggca    1920
gaaatgtgcc tgtcactgag gagaacaaga aggaatacgt ccggctgtat gtgaactgga    1980
ggtttatgag aggaatcgaa gcccagttct tagcacttca aagggggttt aacgaactca    2040
ttccccaaca cttgctgaag ccctttgacc agaaggaact agagctgata ataggtgggc    2100
tggataagat agacctgaac gactggaagt ccaacacccg gctgaaacac tgtgtggcag    2160
acagcaacat cgtcaggtgg ttctggcagg cggtggagac cttcgatgag gagaggagag    2220
ccagactcct gcagtttgtg acaggatcca aagagttcc tctccaaggc ttcaaggctc     2280
tgcaaggctc tacaggcgcg gcagggcccc ggctgttcac cattcacctg atagacgcca    2340
atacagacaa cctgcccaag gcccataccgt gctttaatcg gatcgacatc ccaccctatg    2400
agtcctatga gaagctctat gagaagctgc tgacagcgt ggaggaaacc tgtggctttg     2460
cagtggagtg aagagcagcc agtggccaca gagtcttgct cacaaccacc agacccaaag    2520
catatgcgt ctgcacgcct cccgcgtggc gggctgaggc ctgagattcc agaaaccgag     2580
ggaaaaggct cgtctcctc ctcctttgga gagggcaggc caggggactt tcctaggtgg     2640
ctccccaccca tttattctcc tttattatag tttgcccacc cctccatcac ccatccaata    2700
aaacgcagcc aggtttcgcc ctcagcctcc ttggcacggt gggaaggctg tggtgtctcc    2760
gcgagcatcg acccatggtc aggagccgct gggccgctga gggttgcgtg gtctctgtgc    2820
tagctcccct tgactggagc ctcaaagccc cctttcaagt tcagcagctg ccgacagctt    2880
actgagctca agttccagag gcgtccatca caggctcaca gctgttcag gtagcaggtg     2940
gatttctaag cagcagaagg taaatgcaca gtgtatgctt gctggaactc caccgtggca    3000
ggacactcga ggcaggatgt gttttcccct ttgataggta agggaattgc agcggccgtc    3060
actggaagcc caggtacttc ctttccgcag tatcctggct aaaaagaatg gttttgcaca    3120
```

-continued

```
ggggaaaaaa aaaatcttta aaagtacaat tgttgtgtt ctctacccag tttgaaatta      3180
tcacgtcatg gagctaagca aagaataacc aaaaccagcc tcagaccccc gggtccagct      3240
ctgctcctgt gcctgggat ccggaggctc ctggctgtct tgaaatggac ttttatatgg       3300
ggattgctaa gagctaaact aacagaagag ccttgcacca cagccactgg gcgggacagc      3360
aggagaggcc gctgacctgg gcccctgatg cagctcccca gggtcgggc tgtgcacaaa       3420
gcaggtgtga tggagcgtgt ggcagcaggg tggggtgggg ctttacctcc tacgtggccc      3480
tcgtccccag tggcaacgtg atgctaacag ttctcctcag cttgcttgct tccttgtctt      3540
ctgaggagca aggccaaagc cagcatctct aacacatctc taaccccacg tccaggttgc      3600
acaggcttca cagcgctgac tctcacagca gagcggcagc catgcctccg tttgtggttt      3660
tgttgttttt gtttgtggtg ggggcgagaa cagggtaatt cattagcaag acatttcatt      3720
ggtaccgggt tcaggttgtc tggggaataa tgggaggtcc tgcgggccac cagcttttgt      3780
gttctttctg ttgcttaccc tcaggctggg atagggaag tgtcttccct tctgttcctg       3840
ctgcttctgt ccagtgtggt ctggaagcag ggctgaggtg atggggagtg gattcatagg      3900
tcacatacgc ccccaaccca agaggtttgt ccagcatagg agtcagctgc gctctgggtt      3960
gccaggtctg gggacagaaa ggatgccagg tagacctcac cgcacaagga ccgaacccgc      4020
cccacctccc aggccagact ggggccttac tagtctctca attctgcctt gccccagtag      4080
ggcttctgta cttcatctac cttcatgctt ccgagggtgt tctaaaaccc agctccctcg      4140
tgactctcgg attcaaaagg cgccaggaag cctgtgccct aagtctcagc cagtccacag      4200
gaagcatcca gaccccgcag agtgacacgc ttccggagac tggacacact gcctgttgcc      4260
tttgcacact ggcccagtct gcagggtcct gtgctctgag gatgcactgc aggaatgtca      4320
agtcacactg tttgtgccac ggaagtgatt gggagacaag ccttaggagt cctgtgtcag      4380
atgccctctg aggaagatcc agagcttagg ccctcagggg ctgactgatt ggcgcacata      4440
ccacccactg aggcttctac cagccgttgt gcctgcgtcg cctgtgggtc ccctcattgc      4500
cagttctgag tgtcacaacc tcccaggtct gttcatgtgc agcactgtcc tctgttggta      4560
gcgctgcact tccttgtctg tctaccatgg ttaggcccctt ctgacgcccc tcaaagaaca    4620
ctgcgtggcc agcccacggc acagctcctg gttgccctgc ttgggtctgg gtgaagccct     4680
ttcacgtaag atctcgatcg tcagccctcc tggtggcccc acatcaccca gatgcttcag    4740
gagcctggct ccgcaggctc tcctcaccag cggccggcac ccacactcag ggacgcagca    4800
gacaccactc tactccgcag tgcttcagag aggacgcgcc aggctgcagc agtgctgtgg    4860
cagcaggtcg cagtctcatg cttggttagg aggatctgcc acaaggtgga ttactgaccc    4920
tgcactggct tggccacatg gccaggttca ggtcaggtgg gcgctggact gaccttctgc    4980
agagaacacg ccccaccctat ctgcagcctg tgggccacat ggcagccttc tgacggtgtg   5040
gattttttaaa ctgtgtttat aatgtattct aagttatttt gtaaggtcct gtttgaagtg    5100
ctgctgctag ccctagttgc tctcccagtt tttattgtcc attttcctgt gacagttgta     5160
cactaatgtt ctgtttttatg tcagaatcga aagtatttaa agaaacgcta gttctattta    5220
atgcagttgt ggaaccagct ggaaacacga agcgttgact gtagagcagg ctggacccgg    5280
aaggtcaggt tcatttttgtt acatatgcaa taaactcaca actttacatt ttc            5333
```

<210> SEQ ID NO 40
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 40

Ala Asp Pro Pro Arg Tyr Thr Phe
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ala Pro Pro Pro Ala Asp Ser Ala
 1               5

<210> SEQ ID NO 42
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Pro Leu Pro Pro Gly Trp Glu Glu Arg Thr His Thr Asp Gly Arg
 1               5                  10                  15

Val Phe Phe Ile Asn His Asn Ile Lys Lys Thr Gln Trp Glu Asp Pro
             20                  25                  30

Arg Met

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Pro Pro Gly Trp Asp Glu Tyr Lys Thr His Asn Gly Lys Thr Tyr
 1               5                  10                  15

Tyr Tyr Asn His Asn Thr Lys Thr Ser Thr Trp Thr Asp Pro Arg Met
             20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Leu Pro Ala Gly Trp Glu Met Ala Lys Thr Ser Ser Gly Gln Arg
 1               5                  10                  15

Tyr Phe Leu Asn His Ile Asp Gln Thr Thr Thr Trp Gln Asp Pro Arg
             20                  25                  30

<210> SEQ ID NO 45
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Leu Pro Ala Gly Trp Glu Met Ala Lys Thr Ser Ser Gly Gln Arg
 1               5                  10                  15

Tyr Phe Lys Asn His Ile Asp Gln Thr Thr Thr Trp Gln Asp Pro Arg
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Variable amino acid

<400> SEQUENCE: 46

Pro Leu Pro Ala Gly Trp Glu Met Ala Lys Thr Ser Xaa Gly Gln Arg
 1               5                  10                  15

Tyr Phe Leu Asn His Ile Asp Gln Thr Thr Thr Trp Gln Asp Pro Arg
            20                  25                  30

<210> SEQ ID NO 47
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgcccccgcc gcggacgcag cacggtacac ctttgcac                           38

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtgcaaaggt gtaccgtgct gcgtccgcgg cggggggcg                          38

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggcccggccc tttggggcgg cagcagcagc tgacagcgcc ccgcaac                 47

<210> SEQ ID NO 50
<211> LENGTH: 47
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 50 gttgcgggc gctgtcagct gctgctgccg ccccaaaggg ccgggcc                    47

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgtgaactg tgatgaactt aatcaccagt gccaactc                             38

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gagttggcac tggtgattaa gttcatcaca gttcacac                             38

<210> SEQ ID NO 53
<211> LENGTH: 457
<212> TYPE: PRT
<213> ORGANISM: Homo sapiens

<400> SEQUENCE: 53
```

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu

-continued

```
                195                 200                 205
Pro Trp Pro Gly Pro Thr Ala Pro Ser Pro Thr Ser Arg Pro Pro Trp
    210                 215                 220
Ala Val Asp Pro Ala Phe Ala Glu Arg Tyr Ala Pro Asp Lys Thr Ser
225                 230                 235                 240
Thr Val Leu Thr Arg His Ser Gln Pro Ala Thr Pro Thr Pro Leu Gln
                245                 250                 255
Ser Arg Thr Ser Ile Val Gln Ala Ala Gly Val Pro Gly Gly
                260                 265                 270
Gly Ser Asn Asn Gly Lys Thr Pro Val Cys His Gln Cys His Lys Val
            275                 280                 285
Ile Arg Gly Arg Tyr Leu Val Ala Leu Gly His Ala Tyr His Pro Glu
        290                 295                 300
Glu Phe Val Cys Ser Gln Cys Gly Lys Val Leu Glu Glu Gly Gly Phe
305                 310                 315                 320
Phe Glu Glu Lys Gly Ala Ile Phe Cys Pro Pro Cys Tyr Asp Val Arg
                325                 330                 335
Tyr Ala Pro Ser Cys Ala Lys Cys Lys Lys Ile Thr Gly Glu Ile
            340                 345                 350
Met His Ala Leu Lys Met Thr Trp His Val His Cys Phe Thr Cys Ala
        355                 360                 365
Ala Cys Lys Thr Pro Ile Arg Asn Arg Ala Phe Tyr Met Glu Glu Gly
    370                 375                 380
Val Pro Tyr Cys Glu Arg Asp Tyr Glu Lys Met Phe Gly Thr Lys Cys
385                 390                 395                 400
His Gly Cys Asp Phe Lys Ile Asp Ala Gly Asp Arg Phe Leu Glu Ala
                405                 410                 415
Leu Gly Phe Ser Trp His Asp Thr Cys Phe Val Cys Ala Ile Cys Gln
            420                 425                 430
Ile Asn Leu Glu Gly Lys Thr Phe Tyr Ser Lys Asp Arg Pro Leu
        435                 440                 445
Cys Lys Ser His Ala Phe Ser His Val
    450                 455

<210> SEQ ID NO 54
<211> LENGTH: 153
<212> TYPE: PRT
<213> ORGANISM: Homo sapiens

<400> SEQUENCE: 54

Met Asp Ser Phe Lys Val Val Leu Glu Gly Pro Ala Pro Trp Gly Phe
1               5                   10                  15
Arg Leu Gln Gly Gly Lys Asp Phe Asn Val Pro Leu Ser Ile Ser Arg
                20                  25                  30
Leu Thr Pro Gly Gly Lys Ala Ala Gln Ala Gly Val Ala Val Gly Asp
            35                  40                  45
Trp Val Leu Ser Ile Asp Gly Glu Asn Ala Gly Ser Leu Thr His Ile
        50                  55                  60
Glu Ala Gln Asn Lys Ile Arg Ala Cys Gly Glu Arg Leu Ser Leu Gly
65                  70                  75                  80
Leu Ser Arg Ala Gln Pro Val Gln Ser Lys Pro Gln Lys Ala Ser Ala
                85                  90                  95
Pro Ala Ala Asp Pro Pro Arg Tyr Thr Phe Ala Pro Ser Val Ser Leu
                100                 105                 110
```

```
Asn Lys Thr Ala Arg Pro Phe Gly Ala Pro Pro Ala Asp Ser Ala
        115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150

<210> SEQ ID NO 55
<211> LENGTH: 223
<212> TYPE: PRT
<213> ORGANISM: Homo sapiens

<400> SEQUENCE: 55

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
                20                  25                  30

Leu Thr Pro Gly Gly Lys Ala Ala Gln Ala Gly Val Ala Val Gly Asp
            35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro
    210                 215                 220

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5
```